United States Patent
Pilla

(10) Patent No.: US 10,350,428 B2
(45) Date of Patent: Jul. 16, 2019

(54) METHOD AND APPARATUS FOR ELECTROMAGNETIC TREATMENT OF LIVING SYSTEMS

(71) Applicant: Endonovo Therapeutics, Inc., Woodland Hills, CA (US)

(72) Inventor: Arthur A. Pilla, Oakland, NJ (US)

(73) Assignee: Endonovo Therapetics, Inc., Woodland Hills, CA (US)

( * ) Notice: Subject to any disclaimer, the term of this patent is extended or adjusted under 35 U.S.C. 154(b) by 540 days.

(21) Appl. No.: 14/932,928

(22) Filed: Nov. 4, 2015

(65) Prior Publication Data
US 2016/0121135 A1    May 5, 2016

Related U.S. Application Data

(60) Provisional application No. 62/075,122, filed on Nov. 4, 2014.

(51) Int. Cl.
*A61N 2/00* (2006.01)
*A61N 2/02* (2006.01)

(52) U.S. Cl.
CPC .............. *A61N 2/008* (2013.01); *A61N 2/02* (2013.01)

(58) Field of Classification Search
CPC .......... A61N 2/00; A61N 2/004; A61N 2/008; A61N 2/12
USPC ....................................... 600/9–15
See application file for complete search history.

(56) References Cited

U.S. PATENT DOCUMENTS

| | | | |
|---|---|---|---|
| 1,233,841 A | 7/1917 | Butcher |
| 2,130,758 A | 9/1938 | Rose |
| 2,276,996 A | 3/1942 | Milinowski |
| 2,648,727 A | 8/1953 | Rockwell |

(Continued)

FOREIGN PATENT DOCUMENTS

| | | |
|---|---|---|
| CA | 0608693 | 11/1960 |
| CN | 1052053 A | 6/1991 |

(Continued)

OTHER PUBLICATIONS

Atrophy in Parkinson's Disease, Dr Chris, printed Jun. 24, 2018, pp. 1-3, http://pdring.com/atrophy-in-parkinsons-disease.htm.*

(Continued)

*Primary Examiner* — Samuel G Gilbert
(74) *Attorney, Agent, or Firm* — Roland J. Tong; Manning & Kass, Ellrod, Ramirez, Trester LLP

(57) ABSTRACT

Embodiments of the invention include methods of treating a patient with physiological responses arising from an injury or condition, such as post-operative pain, traumatic brain injury, and cognitive defects. These treatment methods can include the steps of generating a pulsed electromagnetic field from a pulsed electromagnetic field source which is configured to simultaneously increase the rate of ion-dependent signaling, such as CaM/NO/cGMP signaling and to minimize the rate of inhibition of such signaling by natural compounds and applying the pulsed electromagnetic field in proximity to a target region affected by the injury or condition for a first treatment interval followed by an intertreatment period with no electromagnetic field between treatment intervals to reduce a physiological response to the injury or condition.

22 Claims, 8 Drawing Sheets

(56) References Cited

U.S. PATENT DOCUMENTS

| | | |
|---|---|---|
| 3,043,310 A | 7/1962 | Milinowski |
| 3,181,535 A | 5/1965 | Milinowski |
| 3,270,746 A | 9/1966 | Kendall et al. |
| 3,329,148 A | 7/1967 | Kendall |
| 3,329,149 A | 7/1967 | Kendall et al. |
| 3,800,802 A | 4/1974 | Berry et al. |
| 3,890,953 A | 6/1975 | Kraus et al. |
| 3,915,151 A | 10/1975 | Kraus |
| 3,952,751 A | 4/1976 | Yarger |
| 3,978,864 A | 9/1976 | Smith |
| 4,028,518 A | 6/1977 | Boudouris et al. |
| 4,105,017 A | 8/1978 | Ryaby et al. |
| 4,197,851 A | 4/1980 | Fellus |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,340,063 A | 7/1982 | Maurer |
| 4,374,482 A | 2/1983 | Moore et al. |
| 4,428,366 A | 1/1984 | Findl et al. |
| 4,454,882 A | 6/1984 | Takano |
| 4,548,208 A | 10/1985 | Niemi |
| 4,550,714 A | 11/1985 | Talish et al. |
| 4,556,051 A | 12/1985 | Maurer |
| 4,616,629 A | 10/1986 | Moore |
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,765,310 A | 8/1988 | Deagle |
| 4,793,325 A | 12/1988 | Cadossi et al. |
| 4,829,984 A | 5/1989 | Gordon |
| 4,850,372 A | 7/1989 | Ko et al. |
| 4,889,526 A | 12/1989 | Rauscher et al. |
| 4,926,881 A | 5/1990 | Ichinomiya et al. |
| 4,940,453 A | 7/1990 | Cadwell |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,116,304 A | 5/1992 | Cadwell |
| 5,123,898 A | 6/1992 | Liboff et al. |
| 5,147,284 A | 9/1992 | Federov et al. |
| 5,181,902 A | 1/1993 | Erickson et al. |
| 5,224,922 A | 7/1993 | Kurtz |
| 5,314,401 A | 5/1994 | Tepper |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,441,495 A | 8/1995 | Liboff et al. |
| 5,478,303 A | 12/1995 | Foley-Nolan et al. |
| 5,480,373 A | 1/1996 | Fischer et al. |
| 5,518,496 A | 5/1996 | McLeod et al. |
| 5,529,569 A | 6/1996 | Woo |
| 5,584,863 A | 12/1996 | Rauch et al. |
| 5,595,564 A | 1/1997 | Pinna |
| 5,707,334 A | 1/1998 | Young |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,778,894 A | 7/1998 | Dorogi et al. |
| 5,792,209 A | 8/1998 | Varner et al. |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,187 B1 | 5/2001 | Munoz et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,348,070 B1 | 2/2002 | Teissl et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |
| 6,443,883 B1 | 9/2002 | Ostrow et al. |
| 6,450,941 B1 | 9/2002 | Larson |
| 6,458,151 B1 | 10/2002 | Saltiel |
| 6,458,157 B1 | 10/2002 | Suaning et al. |
| 6,463,336 B1 | 10/2002 | Mawhinney |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 | 10/2005 | Simon |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 8,167,784 B1 | 5/2012 | Honeycutt et al. |
| 8,343,027 B1 | 1/2013 | DiMino et al. |
| 8,415,123 B2 | 4/2013 | Pilla et al. |
| 8,961,385 B2 | 2/2015 | Pilla et al. |
| 2001/0007937 A1 | 7/2001 | MacKin |
| 2001/0031906 A1 | 10/2001 | Ishikawa et al. |
| 2001/0041820 A1 | 11/2001 | Woo |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |
| 2003/0158585 A1* | 8/2003 | Burnett .............. A61N 1/36021 607/2 |

(56) References Cited

U.S. PATENT DOCUMENTS

| | | |
|---|---|---|
| 2003/0171640 A1 | 9/2003 | Canedo |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0182287 A1 | 8/2005 | Becker |
| 2005/0215842 A1 | 9/2005 | Pilla et al. |
| 2005/0222625 A1 | 10/2005 | Laniado et al. |
| 2005/0251229 A1 | 11/2005 | Pilla et al. |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2006/0293724 A1 | 12/2006 | Kronberg et al. |
| 2007/0026514 A1 | 2/2007 | Pilla et al. |
| 2007/0043254 A1 | 2/2007 | DeMarco |
| 2007/0060954 A1 | 3/2007 | Cameron et al. |
| 2007/0149901 A1 | 6/2007 | Gordon et al. |
| 2007/0173904 A1 | 7/2007 | Pilla |
| 2007/0203390 A1 | 8/2007 | Rohan et al. |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pilla et al. |
| 2008/0140155 A1 | 6/2008 | Pilla et al. |
| 2008/0200749 A1 | 8/2008 | Zheng et al. |
| 2008/0208287 A1 | 8/2008 | Palermo et al. |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0099623 A1 | 4/2009 | Bentwich |
| 2009/0105781 A1 | 4/2009 | Brighton |
| 2009/0216068 A1 | 8/2009 | Thomas et al. |
| 2009/0326315 A1 | 12/2009 | Nishi et al. |
| 2010/0004500 A1 | 1/2010 | Gliner et al. |
| 2010/0005571 A1 | 1/2010 | Moss et al. |
| 2010/0121407 A1 | 5/2010 | Pfaff et al. |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0184223 A1 | 7/2011 | Peterchev et al. |
| 2011/0190849 A1 | 8/2011 | Faltys et al. |
| 2011/0213195 A1 | 9/2011 | Kraus et al. |
| 2012/0089201 A1 | 4/2012 | Pilla |
| 2012/0116149 A1 | 5/2012 | Pilla et al. |
| 2013/0035539 A1 | 2/2013 | Kornstein |
| 2013/0274540 A1 | 10/2013 | Pilla et al. |
| 2014/0046115 A1 | 2/2014 | Pilla |
| 2014/0046117 A1 | 2/2014 | Pilla |
| 2014/0213843 A1 | 7/2014 | Pilla et al. |
| 2014/0213844 A1 | 7/2014 | Pilla et al. |
| 2014/0303425 A1 | 10/2014 | Pilla et al. |
| 2015/0196771 A1 | 7/2015 | Pilla et al. |
| 2015/0217126 A1 | 8/2015 | Pilla |
| 2015/0297910 A1 | 10/2015 | DiMino et al. |

FOREIGN PATENT DOCUMENTS

| | | |
|---|---|---|
| CN | 1408448 A | 4/2003 |
| CN | 102006793 A | 4/2011 |
| CN | 102151362 A | 8/2011 |
| DE | 970276 | 9/1958 |
| EP | 543152 A2 | 10/1992 |
| EP | 0500983 | 7/1995 |
| EP | 1167070 A1 | 1/2002 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2005/051306 A2 | 6/2005 |
| WO | WO 2008/070001 A2 | 6/2008 |
| WO | WO 2009/155516 | 12/2009 |
| WO | WO 2010/067336 A2 | 6/2010 |
| WO | WO 2011/053607 A1 | 5/2011 |

OTHER PUBLICATIONS

Aaron et al.; Power frequency fields promote cell differentiation coincident with an increase in transforming growth factor-?1 expression; Bioelectromagnetic; vol. 20 (7); pp. 453-458; Oct. 1999.

Aaron et al.; The conservative treatment of osteonecrosis of the femoral head. A comparison of core decompression and pulsing electromagnetic fields; Clin. Orthopaed. Rel. Res.; vol. 249; pp. 209-218; Dec. 1989.

Adair; A physical analysis of the ion parametric resonance model; Bioelectromagnetics; vol. 19(3); pp. 181-191; Dec. 1998.

Adair; Comment: Analyses of Models of Ion Actions Under the Combined Action of AC and DC Magnetic Fields; Bioelectromagnetics; vol. 27; No. 4; pp. 332-334; May 2006.

Adair; Criticism of Lednev's mechanism for the influence of weak magnetic fields on biological systems; Bioelectromagnetics; vol. 13 (3); pp. 231-235; Feb. 1992.

Adair; Static and low-frequency magnetic field effects: Health risks and therapies; Rep Prog Phys; vol. 63 (3); pp. 415-454; Mar. 2000.

Akai et al.; Effect of electrical stimulation on musculoskeletal systems: a meta-analysis of controlled clinical trials; Bioelectromagnetics; vol. 23 (2); pp. 132-143; Feb. 2002.

Albensi et al.; Diffusion and high resolution MRI of traumatic brain injury in rats: time course and correlation with histology. Exp Neurol 162, 61-72 (Mar. 2000).

Anderson et al.; Fluoro-jade B stains quiescent and reactive astrocytes in the rodent spinal cord. J Neurotrauma 20, 1223-31 (Nov. 2003).

Arendash et al.; Electromagnetic Field Treatment Protects Against and Reverses Cognitive Impairment in Alzheimer's Disease Mice. Journal of Alzheimer's Disease vol. 19, 191-210 (Jan. 2010).

Armonda et al.; Wartime traumatic cerebral vasospasm: recent review of combat casualties. Neurosurgery 59, 1215-25; discussion 1225 (Dec. 2006).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Auffray et al.; Blood monocytes: development, heterogeneity, and relationship with dendritic cells. Annu Rev Immunol 27, 669-92 (Jan. 2009).

Ayrapetyan et al.; Magnetic fields alter electrical properties of solutions and their physiological effects; Bioelectromagnetics; vol. 15 (2); pp. 133-142; (year of pub. sufficiently earlier than effective US filing date and any foreign priority date) 1994.

Barger et al.; Microglial Activation by Alzheimer Amyloid Precursor Protein and Modulation by Apolipoprotein E. Nature; vol. 388; 878-881 (Aug. 1997).

Bassett et al.; A non-operative salvage of surgically-resistant pseudoarthroses and non-unions by pulsing electromagnetic fields; Clin Orthop; vol. 124; pp. 117-131; May 1977.

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Batchelor et al.; Exquisite sensitivity to subsecond, picomolar nitric oxide transients conferred on cells by guanylyl cyclase-coupled receptors; Proc. Natl. Acad. Sci. U.S.A.; 107(51); pp. 22060-22065; Dec. 21, 2010.

Bawin et al.; Effects of modulated VHF fields on the central nervous system; Ann NY Acad Sci; vol. 247; pp. 74-81; Feb. 1975.

(56) References Cited

OTHER PUBLICATIONS

Bawin et al.; Sensitivity of calcium binding in cerebral tissue to weak environmental electric fields oscillating at low frequency; Proc Nat''l Acad Sci, USA; 73(6); pp. 1999-2003; Jun. 1976.
Bearden Jr.; Quantitation of submicrogram quantities of protein by an improved protein-dye binding assay; Biochim Biophys Acta; vol. 533(2); pp. 525-529; Apr. 26, 1978.
Beaumont et al.; The effects of human corticotrophin releasing factor on motor and cognitive deficits after impact acceleration injury. Neurol Res 22, 665-73 (Oct. 2000).
Beaumont et al.; The impact-acceleration model of head injury: injury severity predicts motor and cognitive performance after trauma. Neurol Res 21, 742-54 (Dec. 1999).
Beck et al.; The Bioelectromagnetics Society (History of the first 25 years); eds. Shappard, A. and Blackman, C.; 46 pgs.; (year of publication is sufficiently earlier than the effective U.S. filing date and any foreign priority date) 2004.
Becker, T. O.; The bioelectric factors in amphibian limb regeneration. J. Bone Joint Surg. 43A, 643 (Jul. 1961).
Bederson et al.; Nuclear magnetic resonance imaging and spectroscopy in experimental brain edema in a rat model. J Neurosurg 64, 795-802 (May 1986).
Belanger et al.; Cognitive sequelae of blast-related versus other mechanisms of brain trauma. J Int Neuropsychol Soc 15(1), 1-8 (Jan. 2009).
Belyaev et al.; Frequency-dependent Effects ofELF Magnetic Field on Cromatin Conformation in *Escherichia coli* Cells and Human Lymphocytes; Biochimica et Biophysica Acta; vol. 1526(3); pp. 269-276; Jun. 15, 2001.
Binder et al.; Pulsed electromagnetic field therapy of persistent rotator cuff tendinitis: a double blind controlled assessment; Lancet; vol. 1 (8379); pp. 695-697; Mar. 31, 1984.
Binshtok et al.; Nociceptors are interleukin-1 beta sensors; J. Neurosci.; 28(52); pp. 14062-14073; Dec. 24, 2008.
Blackman et al.; A role for the magnetic field in the radiation induced efflux of calcium ions from brain tissue in vitro; Bioelectromagnetics; vol. 6(4); pp. 327-337; (year of pub. sufficiently earlier than effective US filing date and any foreign priority date) 1985.
Blackman et al.; Action of 50 Hz magnetic fields on neurite outgrowth in pheochromocytoma cells. Bioelectromagnetics 14, 273-86 (year of publication is sufficiently earlier than the effective U.S. filing date and any foreign priority date) (1993).
Blackman et al.; Effects of ELF fields on calcium-ion efflux from brain tissue in vitro; Radiat Res; vol. 92(3); pp. 510-520; Dec. 1982.
Blackman et al.; Empirical test of an ion parametric resonance model for magnetic field interactions with PC-12 cells; Bioelectromagnetics; vol. 15(3): pp. 239-260; (year of pub. sufficiently earlier than effective US filing date and any foreign priority date) 1994.
Blackman et al.; Influence of electromagnetic fields on the efflux of calcium ions from brain tissue in vitro: A three-model analysis consistent with the frequency response up to 510 Hz; Bioelectromagnetics; vol. 9(3); pp. 215-227; (year of pub. sufficiently earlier than effective US filing date and any foreign priority date) 1988.
Blackman et al.; Multiple power-density windows and their possible origin; Bioelectromagnetics; vol. 10(2); pp. 115-128; (year of pub. sufficiently earlier than effective US filing date and any foreign priority date) 1989.
Blanchard et al.; Clarification and application of an ion parametric resonance model for magnetic field interactions with biological systems; Bioelectromagnetics; vol. 15(3); pp. 217-238; (year of pub. sufficiently earlier than effective US filing date and any foreign priority date) 1994.
Blank et al.; Do electromagnetic fields interact directly with DNA?; Bioelectromagnetics; vol. 18(2); pp. 111-115; (year of pub. sufficiently earlier than effective US filing date and any foreign priority date) 1997.
Blumenthal et al.; Effects of low-intensity AC and/or DC electromagnetic fields on cell attachment and induction of apoptosis; Bioelectromagnetics; vol. 18(3); pp. 264-272; (year of pub. sufficiently earlier than effective US filing date and any foreign priority date) 1997.
Bodian et al.; The visual analog scale for pain: clinical significance in postoperative patients; Anesthesiology; 95(6); pp. 1356-1361; Dec. 2001.
Borbely et al.; Pulsed high-frequency electromagnetic field affects human sleep and sleep electroencephalogram. Neurosci Lett 275, 207-10 (Nov. 19, 1999).
Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).
Bredt, D. S.; Nitric oxide signaling specificity-the heart of the problem. J Cell Sci 116, 9-15 (Jan. 2003).
Brighton et al.; Signal transduction in electrically stimulated bone cells. J Bone Joint Surg Am 83-A, 1514-23 (Oct. 2001).
Brighton, C. T.; The treatment of non-unions with electricity. J Bone Joint Surg Am 63, 847-51 (Jun. 1981).
Brooks et al.; Magnetic resonance spectroscopy in traumatic brain injury. J Head Trauma Rehabil 16, 149-64 (Apr. 2001).
Burton, T.; New Test for Brain Injury on Horizon, The Wall Street Journal, New York, (Jul. 20, 2010).
Cain; Stimulating Treatment; Orthopedic Technology Review; vol. 4; No. 4; pp. 31-34; Jul.-Aug. 2002.
Cammermeyer, J.; I. An evaluation of the significance of the "dark" neuron. Ergeb Anat Entwicklungsgesch 36, 1-61 (year of publication is sufficiently earlier than the effective U.S. filing date and any foreign priority date) (1962).
Canals et al.; Neurotrophic and neurotoxic effects of nitric oxide on fetal midbrain cultures. J Neurochem 76, 56-68 (Jan. 2001).
Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.
Casper et al.; Dopaminergic neurons associate with blood vessels in neural transplants. Exp Neurol 184, 785-93 (Dec. 2003).
Casper et al.; Enhanced vascularization and survival of neural transplants with ex vivo angiogenic gene transfer. Cell Transpl. 11, 331-349 (year of publication is sufficiently earlier than the effective U.S. filing date and any foreign priority date) (2002).
Cederberg et al.; What has inflammation to do with traumatic brain injury? Childs Nery Syst 26, 221-6 (Feb. 2010).
Cernak et al.; Cognitive deficits following blast injury-induced neurotrauma: possible involvement of nitric oxide. Brain Inj 15, 593-612 (Jul. 2001).
Cernak et al.; Traumatic brain injury: an overview of pathobiology with emphasis on military populations. J Cereb Blood Flow Metab 30, 255-66 (Feb. 2010).
Cernak et al.; Ultrastructural and functional characteristics of blast injury-induced neurotrauma. J Trauma 50, 695-706 (Apr. 2001).
Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.
Chiabrera et al.; Effect of Lifetimes on Ligand Binding Modelled by the Density Operator; Bioelectrochemistry and Bioenergetics; vol. 30; pp. 35-42; Mar. 1993.
Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.
Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.
Chung et al.; The nuts and bolts of low-level laser (light) therapy; Ann. Biomed. Eng.; 40(2); pp. 516-533; Feb. 2012 (author Manuscript).
Ciani et al.; Akt pathway mediates a cGMP-dependent survival role of nitric oxide in cerebellar granule neurones. J Neurochem 81, 218-28 (Apr. 2002).

(56) References Cited

OTHER PUBLICATIONS

Clapham, D.; Calcium signaling; Cell; vol. 80; pp. 259-268; Jan. 27, 1995.
Clausen et al.; Neutralization of interleukin-1? modifies the inflammatory response and improves histological and cognitive outome following traumatic brain injury in mice. European Journal of Neuroscience; vol. 30; pp. 385-396; Aug. 30, 2009.
Colbert et al.; Magnetic mattress pad use in patients with fibromyalgia: A randomized double-blind pilot study; J Back Musculoskeletal Rehab; vol. 13(1); 19-31; Jan. 1999.
Coll et al.; Postoperative pain assessment tools in day surgery: literature review; J. Adv. Nurs.; 46(2); pp. 124-133; Apr. 2004.
Collacott et al.; Bipolar permanent magnets for the treatment of low back pain: A pilot study; JAMA; vol. 283; No. 10; pp. 1322-1325; Mar. 8, 2000.
Colomer et al.; Physiological roles of the Ca2+/CaM-dependent protein kinase cascade in health and disease. Subcell Biochem 45, 169-214 (year of publication is sufficiently earlier than the effective U.S. filing date and any foreign priority date) (2007).
Cook et al.; Resting EEG is affected by exposure to a pulsed ELF magnetic field. Bioelectromagnetics 25, 196-203 (Apr. 2004).
Cook et al.; The effects of pulsed, high-frequency radio waves on the rate of osteogenesis in the healing of extraction wounds in dogs; Oral Sug.; 32(6); (Dec. 1971).
Cork et al.; Computer-aided analysis of polarized neurite growth. Effects of applied electrical fields on neuronal development. J Neurosci Methods 32, 45-54 (Apr. 1990).
Courtney et al.; A thoracic mechanism of mild traumatic brain injury due to blast pressure waves. Med Hypotheses 72, 76-83 (Jan. 2009).
Cox, J.; Interactive Properties of Calmodulin; Biochem J.; vol. 249(3); pp. 621-629; Feb. 1, 1988.
Crocetti et al.; Low intensity and frequency pulsed electromagnetic fields selectively impair breast cancer cell viability; Plos One; 8(9); p. e72944; 13 pages; Sep. 11, 2013.
Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).
Czosnyka, et al.; Montoring and Interpretation of Intracranial Pressure. J. Neurol Neurosurg Psychiatry; vol. 75, 813-821; (Jun. 2004).
De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).
Delle Monache et al.; Extremely low frequency electromagnetic fields (ELF-EMFs) induce in vitro angiogenesis process in human endothelial cells; Bioelectromagnetics; 29; pp. 640-648; Mar. 5, 2008.
Dixon et al.; A controlled cortical impact model of traumatic brain injury in the rat. J Neurosci Methods 39, 253-62 (Oct. 1991).
Dixon et al.; A fluid percussion model of experimental brain injury in the rat. J Neurosurg 67, 110-9 (Jul. 1987).
Edmonds, D.; Larmor precession as a mechanism for the detection of static and alternating magnetic fields; Bioelectrochemistry and Bioenergetics; vol. 30; pp. 3-12; Mar. 1993.
Edwards et al.; Final results of MRC CRASH, a randomised placebo controlled trial of intravenous corticosteroid in adults with head injury-outcomes at 6 months. Lancet 365, 1957-9 (Jun. 2005).
Elder et al.; Blast-related mild traumatic brain injury: mechanisms of injury and impact on clinical care. Mt Sinai J Med 76, 111-8 (Apr. 2009).
Elder et al.; Increased locomotor activity in mice lacking the low-density lipoprotein receptor. Behav Brain Res 191, 256-65 (Aug. 2008).
Engström, S.; Dynamic properties of Lednev's parametric resonance mechanism; Bioelectromagnetics; vol. 17(1); pp. 58-70; (year of pub. sufficiently earlier than effective US filing date and any foreign priority date) 1996.

Fabre et al.; Antidepressant efficacy and cognitive effects of repetitive transcranial magnetic stimulation in vascular depression: an open trial. Int J Geriatr Psychiatry 19, 833-42 (Sep. 2004).
Farndale et al.; The action of pulsed magnetic fields on cyclic AMP levels in cultured fibroblasts. Biochim Biophys Acta 881, 46-53 (Mar. 19, 1986).
Farrarelli et al.; Breakdown in cortical effective connectivity during midazolam-induced loss of consciousness. Proc Natl Acad Sci U S A 107, 2681-6 (Feb. 9, 2010).
Fassbender et al.; Temporal profile of release of interleukin-1beta in neurotrauma. Neurosci Lett 284, 135-8 (Apr. 2000).
Faul et al.; Traumatic brain injury in the United States (Emergency department visits, hospitalization and deaths 2002-2006); U.S. Dept. Of Health and Human Services, 74 pgs.; Mar. 2010.
Fetler et al.; Brain under surveillance: the microglia patrol. Science 309, 392-3 (Jul. 15, 2005).
Fitzsimmons et al.; A pulsing electric field (PEF) increases human chondrocyte proliferation through a transduction pathway involving nitric oxide signaling. J Orthop Res 26, 854-9 (Jun. 2008).
Fitzsimmons et al.; Combined magnetic fields increase net calcium flux in bone cells. Calcif. Tiss. Intl.; vol. 55; pp. 376-380; Nov. 1994.
Foda et al.; A new model of diffuse brain injury in rats. Part II: Morphological characterization. J Neurosurg 80, 301-13 (Feb. 1994).
Foley-Nolan et al.; Pulsed high frequency (27MHz) electromagnetic therapy for persistent neck pain. A double blind, placebo-controlled study of 20 patients. Orthopedics 13, 445-51 (Apr. 1990).
Friedman et al.; Quantitative proton MRS predicts outcome after traumatic brain injury. Neurology 52, 1384-91 (Apr. 1999).
Fukada et al.; On the piezoelectric effect of bone. J Phys Soc Japan 12(10), 1158-1162 (Oct. 1957).
Gaetz, M.; The neurophysiology of brain injury. Clin Neurophysiol 115, 4-18 (Jan. 2004).
Garthwaite et al.; Cyclic GMP and cell death in rat cerebellar slices. Neuroscience 26, 321-6 (Jul. 1988).
Gasparovic et al.; Decrease and recovery of N-acetylaspartate/creatine in rat brain remote from focal injury. J Neurotrauma 18, 241-6 (Mar. 2001).
Ghirnikar et al.; Inflammation in traumatic brain injury: role of cytokines and chemokines. Neurochem Res 23, 329-40 (Mar. 1998).
Ginsberg, A. J.; Ultrashort radio waves as a therapeutic agent. Med Record 140, 651-653 (Dec. 19, 1934).
Glass et al.; Mechanisms underlying inflammation in neurodegeneration. Cell 140, 918-34 (Mar. 19, 2010).
Goligorsky et al.; Relationships between caveolae and eNOS: everything in proximity and the proximity of everything; Am J Physiol Renal Physiol; 283; pp. F1-F10; Jul. 2002.
Gona et al.; Effects of 60 Hz electric and magnetic fields on the development of the rat cerebellum. Bioelectromagnetics 14, 433-47 (year of publication is sufficiently earlier than the effective U.S. filing date and any foreign priority date) (1993).
Goodwin et al.; A double-blind study of capacitively coupled electrical stimulation as an adjunct to lumbar spinal fusions(printed from online source). Spine 24(13), 1349-1357 (Jul. 1999).
Graeber et al.; New expression of myelomonocytic antigens by microglia and perivascular cells following lethal motor neuron injury. J Neuroimmunol 27, 121-32 (May 1990).
Greenebaum et al.; Effects of pulsed magnetic fields on neurite outgrowth from chick embryo dorsal root ganglia. Bioelectromagnetics 17, 293-302 (year of publication is sufficiently earlier than the effective U.S. filing date and any foreign priority date) (1996).
Guo et al.; Meta-analysis of clinical efficacy of pulsed radio frequency energy treatment; Ann. Surg.; 255;(3); pp. 457-467; Mar. 2012.
Ha et al.; Nitric oxide prevents 6-hydroxydopamine induced apoptosis in PC12 cells through cGMP-dependent PI3 kinase/AKT activation; FASEB J.; 17(9); pp. 1036-1047; Jun. 2003.
Halle, B.; On the cyclotron resonance mechanism for magnetic field effects on transmembrane ion conductivity; Bioelectromagnetics; vol. 9(4); pp. 381-385; (year of pub. sufficiently earlier than effective US filing date and any foreign priority date) 1988.
Hart, F.; A quantum mechanical model for bioelectromagnetic resonance phenomena; J Bioelectr; vol. 9; pp. 1-7; Jan. 1990.

(56) References Cited

OTHER PUBLICATIONS

Heden et al.; Effects of pulsed electromagnetic fields on postoperative pain: a double-blind randomized pilot study in breast augmentation patients; Aesthet. Plast. Surg.; 32; pp. 660-666; Jul. 2008.

Hellmich et al.; Dose-dependent neuronal injury after traumatic brain injury; Brain Research; 1044; pp. 144-154 (May 2005).

Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).

Ignarro et al.; Heme-dependent activation of guanylate cyclase by nitric oxide: a novel signal transduction mechanism. Blood Vessels 28, 67-73 (Nov.-Dec. 1991).

Ito et al.; Characterization of edema by diffusion-weighted imaging in experimental traumatic brain injury. J Neurosurg 84, 97-103 (Jan. 1996).

Itoh et al.; Accelerated wound healing of pressure ulcers by pulsed high peak power electromagnetic energy (Diapulse). Decubitus 4(1), pp. 24-25, 29-30, 32 & 34 (Feb. 1991).

Jackson et al.; The demonstration of new human brain-specific proteins by high-resolution two-dimensional polyacrylamide gel electrophoresis. J Neurol Sci 49, 429-38; (Mar. 1981).

Jenrow et al.; Weak ELF magnetic field effects on hippocampal rhythmic slow activity. Exp Neurol 153, 328-34 (Oct. 1998).

Johansson, et al.; Brij 58, a polyoxethylene acyl ether, creates membrane vesicles of uniform sidedness: A new tool to obtain inside-out (cytoplasmic side-out) plasma membrane vesicle; Plant J.; vol. 7(1); pp. 165-173; Jan. 1995.

Jokela et al.; Assessment of the magnetic field exposure due to the battery current of digital mobile phones. Health Phys 86, 56-66 (Jan. 2004).

Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-97; Oct. 31, 1987.

Jortner, B. S.; The return of the dark neuron. A histological artifact complicating contemporary neurotoxicologic evaluation. Neurotoxicology 27, 628-34 (Jul. 2006).

Kamm et al.; The effect of traumatic brain injury upon the concentration and expression of interleukin-1beta and interleukin-10 in the rat. J Trauma 60, 152-7 (Jan. 2006).

Kanje et al.; Pretreatment of rats with pulsed electromagnetic fields enhances regeneration of the sciatic nerve. Bioelectromagnetics 14, 353-9 (year of publication is sufficiently earlier than the effective U.S. filing date and any foreign priority date) (1993).

Kehlet et al.; Evidence-based surgical care and the evolution of fast-track surgery; Ann. Surg.; 248(2); pp. 189-198; Aug. 2008.

Kimura et al.; Reciprical regulation between nitric oxide and vascular endothelial growth factor in angiogenesis; Acta Biochimica Polonica; vol. 50, No. 1; pp. 49-59; (year of publication is sufficiently earlier than the effective U.S. filing date and any foreign priority date) 2003.

Kingham et al.; Microglial secreted cathepsin B induces neuronal apoptosis. J Neurochem 76, 1475-84 (Mar. 2001).

Kjellbom et al.; Preparation and polypeptide composition of chlorophyll-free plasma membranes from leaves of light-grown spinach and barley; Physiol Plant; vol. 62; pp. 501-509; Dec. 1984.

Klit et al.; Central post-stroke pain: clinical characteristics, pathophysiology, and management; Lancet Neurol.; 8(9); pp. 857-868; Sep. 2009.

Kloth et al.; Effect of Pulsed Radio Frequency Stimulation on Wound Healing: A Double-Blind Pilot Clinical Study; in "Electricity and Magnetism in Biology and Medicine"; Bersani F, ed,, Plenum, New York; pp. 875-878; (year of pub. sufficiently earlier than effective US filing date and any foreign priority date) 1999.

Knowles et al.; Nitric oxide synthases in mammals. Biochem J 298, 249-58 (Mar. 1994).

Koch, et al.; Interaction between weak low-frequency magnetic fields and cell membranes; Bioelectromagnetics; vol. 24(6); pp. 39-402; Sep. 2003.

Körner et al.; Surface properties of right side-out plasma membrane vesicles isolated from barley roots and leaves; Plant Physiol.; vol. 79(1); pp. 72-79; Sep. 1985.

Kossmann et al.; Intrathecal and serum interleukin-6 and the acute-phase response in patients with severe traumatic brain injuries. Shock 4, 311-7 (Nov. 1995).

Kramarenko et al.; Effects of high-frequency electromagnetic fields on human EEG: a brain mapping study. Int J Neurosci 113, 1007-19 (Jul. 2003).

Lai et al.; Magnetic-field-induced DNA strand breaks in brain cells of the rat. Environ Health Perspect 112, 687-94 (May 2004).

Langlois et al.; The epidemiology and impact of traumatic brain injury: a brief overview. J Head Trauma Rehabil 21, 375-8 (Aug. 2006).

Lansdown et al.; Sequential changes in trace metal, metallothionein and calmodulin concentrations in healing skin wounds; J. Anat.; vol. 195(Pt 3); pp. 375-386; Oct. 1999.

Larsson et al.; Isolation of highly purified plant plasma membranes and separation of inside-out and rightside-out vesicles; Methods Enzymol; vol. 228; pp. 451-469; (year of pub. sufficiently earlier than effective US filing date and any foreign priority date) 1994.

Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.

Lednev, V.; Possible mechanism for the influence of weak magnetic fields on biological systems; Bioelectromagnetics; vol. 12; pp. 71-75; (year of publication is sufficiently earlier than the effective U.S. filing date and any foreign priority date) 1991.

LeDoux, J.; Emotion: clues from the brain. Annu Rev Psychol 46, 209-35 (Jan. 1995).

Lee et al.; Nitric oxide in the healing wound: a time-course study. J Surg Res 101, 104-8 (Nov. 2001).

Lee et al.; Pulsed magnetic and electromagnetic fields in experimental achilles tendonitis in the rat: a prospective randomized study. Arch Phys Med Rehabil 78, 399-404 (Apr. 1997).

Lescot et al.; Temporal and regional changes after focal traumatic brain injury. J Neurotrauma 27, 85-94 (Jan. 2010).

Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296 Oct. 31, 1987.

Liboff, et al.; Geomagnetic cyclotron resonance in living cells; J Biol Phys; vol. 13(4); pp. 99-102; Dec. 1985.

Liboff, et al.; Kinetics of channelized membrane ions in magnetic fields; Bioelectromagnetics; vol. 9(1); pp. 39-51; (year of pub. sufficiently earlier than effective US filing date and any foreign priority date) 1988.

Lighthall, J. W.; Controlled cortical impact: a new experimental brain injury model. J Neurotrauma 5, 1-15 (year of publication is sufficiently earlier than the effective U.S. filing date and any foreign priority date) (1988).

Likic et al.; Dynamics of Ca2+-saturated Calmodulin D129N Mutant Studied by Multiple Molecular Dynamics Simulations; Protein Sci; vol. 12(10); pp. 2215-2229; Oct. 2003.

Lincoln et al.; Low frequency of pathogenic mutations in the ubiquitin carboxy-terminal hydrolase gene in familial Parkinson's disease. Neuroreport 10, 427-9 (Feb. 1999).

Ling et al.; Explosive blast neurotrauma. J Neurotrauma 26, 815-25 (Jun. 2009).

Linovitz et al.; Combined magnetic fields accelerate and increase spine fusion: a double-blind, randomized, placebo controlled study(printed from online source). Spine 27, 1383-1389 (Jul. 2002).

Liu et al.; Efficacy of continuous wound catheters delivering local anesthetic for postoperative analgesia: a quantitative and qualitative systematic review of randomized controlled trials; J. Am. Coll. Surg.; 203(6); pp. 914-932; Dec. 31, 2006.

Liu et al.; Ubiquitin C-terminal hydrolase-L1 as a biomarker for ischemic and traumatic brain injury in rats (Author Manuscript). Eur J Neurosci 31(4), 722-32 (Feb. 2010).

(56) References Cited

OTHER PUBLICATIONS

Louin et al.; Selective inhibition of inducible nitric oxide synthase reduces neurological deficit but not cerebral edema following traumatic brain injury. Neuropharmacology 50, 182-90 (Feb. 2006).
Lukas, T.; A Signal Transduction Pathway Model Prototype II: Application to Ca2+-Calmodulin Signaling and Myosin Light Chain Phosphorylatiori; Biophysical Journal; vol. 87(3); pp. 1417-1425; Sep. 2004.
Maas et al.; Moderate and severe traumatic brain injury in adults. Lancet Neural 7, 728-41 (Aug. 2008).
Maas et al.; Prognosis and clinical trial design in traumatic brain injury: the IMPACT study. J Neurotrauma 24, 232-8 (Feb. 2007).
Maas et al.; Why have recent trials of neuroprotective agents in head injury failed to how convincing efficacy? A pragmatic analysis and theoretical considerations. (printed from online source) Neurosurgery 44, 1286-98 (Jun. 1999).
Madhusoodanan et al.; NO-cGMP signaling and regenerative medicine involving stem cells. Neurochem Res 32, 681-94 (Apr.-May 2007).
Maeda et al.; Effect of water on piezoelectric, dielectric, and elastic properties of bone; Biopolymers 21(10); 2055-2068 (Oct. 1982).
Man, et al.; The influence of permanent magnetic field therapy on wound healing in suction lipectomy patients: A double-blind study; Plastic and Reconstructive Surgery; vol. 104(7); pp. 2261-2296; Dec. 1999 (printed Jul. 17, 2010).
Markov, et al.; Weak static magnetic field modulation of myosin phosphorylation in a cell-free preparation: Calcium dependence; Bioelectrochemistry and Bioenergetics; vol. 43(2); pp. 233-238; Aug. 1997.
Marmarou et al.; A new model of diffuse brain injury in rats. Part I: Pathophysiology and biomechanics. J Neurosurg 80, 291-300 (Feb. 1994).
Martin et al.; Parkinson's disease alpha-synuclein transgenic mice develop neuronal mitochondrial degeneration and cell death. J Neurosci 26, 41-50 (Jan. 2006).
McDonald, F.; Effect of static magnetic fields on osteoblasts and fibroblasts in-vitro; Bioelectromagnetics; vol. 14(3); pp. 187-196; (year of pub. sufficiently earlier than effective US filing date and any foreign priority date) 1993.
McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).
McIntosh et al.; Traumatic brain injury in the rat: characterization of a lateral fluid-percussion model. Neuroscience 28(1), 233-44 (year of publication is sufficiently earlier than the effective U.S. filing date and any foreign priority date) (1989).
McIntosh et al.; Traumatic brain injury in the rat: characterization of a midline fluid-percussion model. Cent Nerv Syst Trauma 4, 119-34 (year of publication is sufficiently earlier than the effective U.S. filing date and any foreign priority date) (1987).
McLean, et al.; Blockade of sensory neuron action potentials by a static magnetic field in the 10 mT range; Bioelectromagnetics; vol. 16(1); pp. 20-32; (year of pub. sufficiently earlier than effective US filing date and any foreign priority date) 1995.
McLeod, et al.; Dynamic characteristics of membrane ions in multifield configurations of low-frequency electromagnetic radiation; Bioelectromagnetics; vol. 7(2); pp. 177-189; (year of pub. sufficiently earlier than effective US filing date and any foreign priority date) 1986.
Mehler, et al.; Structural Dynamics of Calmodulin and Troponin C; Protein Engineering; vol. 4; No. 6; pp. 625-627; Aug. 1991.
Mellor, S.; The pathogenesis of blast injury and its management. Br J Hosp Med 39, 536-9 (Jun. 1988).
Miller et al.; Role of Ca2+/calmodulinstimulated cyclic nucleotide phosphodiesterase 1 in mediating cardiomyocyte hypertrophy; Circ. Res.; 105(10); pp. 956-964; Nov. 6, 2009.
Mo et al.; Kinetics of a cellular nitric oxide/cGMP/phosphodiesterase-5 pathway; J. Biol. Chem.; 279(25); pp. 26149-26158; Jun. 18, 2004.

Mont et al.; Pulsed electrcial stimulation to defer TKA in patients with knee osteoarthritis; The Cutting Edge; 29(10); pp. 887-892 (Oct. 2006).
Mooney; A randomized double blind prospective study of the efficacy of pulsed electromagnetic fields for interbody lumbar fusions; Spine; vol. 15(7); pp. 708-715; Jul. 1990.
Morganti-Kossmann et al.; Production of cytokines following brain injury: beneficial and deleterious for the damaged tissue. Mol Psychiatry 2, 133-6 (Mar. 1997).
Morris et al.; Place navigation impaired in rats with hippocampal lesions. Nature 297, 681-3 (Jun. 1982).
Muehsam et al.; Lorentz Approach to Static Magnetic Field Effects on Bound Ion Dynamics and Binding Kinetics: Thermal Noise Considerations; Bioelectromagnetics; vol. 17(2); pp. 89-99; (year of pub. sufficiently earlier than effective US filing date and any foreign priority date) 1996.
Muehsam et al.; Weak Magnetic Field Modulation of Ion Dynamics in a Potential Well: Mechanistic and Thermal Noise Considerations; Bioelectrochem. & Bioenergetics; vol. 35; pp. 71-79; Nov. 1994.
Muehsam, et al.; The sensitivity of cells and tissues to exogenous fields: effects of target system initial state; Bioelectrochemistry and Bioenergetics; vol. 48(1); pp. 35-42; Feb. 1999.
Naldini et al.; Role of inflammatory mediators in angiogenesis. Curr Drug Targets Inflamm Allergy 4, 3-8 (Feb. 2005).
Nara, et al.; Fourier Transform Infrared Spectroscopic Study on the Ca2+-bound Coordination Structures of Synthetic Peptide Analogues of the Calcium-binding Site III of Troponin C; Biopolymers; vol. 82; issue 4; pp. 339-343; Jul. 2006.
Narayan et al.; Clinical trials in head injury (Author Manuscript). J Neurotrauma 19, 503-57 (May 2002).
Nauta et al.; Silver impregnation of degenerating axons in the central nervous system: a modified technic. Stain Technol 29, 91-3 (Mar. 1954).
Neff; Using pulsed energy therapy for brain injury and concussion; The Headliner; vol. X; Issue 4; pp. 14; Fall 2008.
Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).
Oda et al.; Magnetic field exposure saves rat cerebellar granule neurons from apoptosis in vitro. Neurosci Lett 365, 83-6 (Jul. 22, 2004).
Ohkubo et al.; Acute effects of static magnetic fields on cutaneous microcirculation in rabbits; In Vivo; vol. 11; pp. 221-226; May-Jun. 1997.
Okano et al.; Biphasic effects of static magnetic fields on cutaneous microcirculation in rabbits; Bioelectromagnetics; vol. 20(3); pp. 161-171; (year of publication is sufficiently earlier than the effective U.S. filing date and any foreign priority date) 1999.
Okie, S.; Traumatic brain injury in the war zone. N Engl J Med 352, 2043-7 (May 19, 2005).
Olbe et al.; The spinach plasma membrane Ca2þ pump is a 120-kDa polypeptide regulated by calmodulinbinding to a terminal region; Physiol Plantarum; vol. 103; pp. 35-44; May 1998.
Panagopoulos et al.; Evaluation of specific absorption rate as a dosimetric quantity for electromagnetic fields bioeffects; Plos One; 8(6); p. e62663; 9 pages; Jun. 4, 2013.
Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).
Papa et al.; Ubiquitin C-terminal hydrolase is a novel biomarker in humans for severe traumatic brain injury. Crit Care Med 38, 138-44 (Jan. 2010).
Pascual et al.; Time course of early metabolic changes following diffuse traumatic brain injury in rats as detected by (1)H NMR spectroscopy. J Neurotrauma 24, 944-59 (Jun. 2007).
Patino et al.; Pulsed electromagnetic fields in experimental cutaneous wound healing in rats. J Burn Care Rehabil 17, 528-31 (Nov./Dec. 1996).
Paylor et al.; Inbred strain differences in prepulse inhibition of the mouse startle response. Psychopharmacology (Berl) 132, 169-80 (Jul. 1997).

(56) References Cited

OTHER PUBLICATIONS

Pennington et al.; Pulsed, non-thermal, high-frequency electromagnetic energy (DIAPULSE) in the treatment of grade I and grade II ankle sprains. Mil Med 158, 101-4 (Feb. 1993).

Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 33, 393-403, in press, Epub ahead of print (Apr. 2010).

Pilla et al.; EMF signals and ion/ligand binding kinetics:prediction of bioeffective waveform parameters; Bioelectrochemistry and Bioenergetics; vol. 48(1); pp. 27-34; Feb. 1999.

Pilla et al.; Gap junction impedance tissue dielectrics and thermal noise limits for electromagnetic field bioeffects; Bioelectrochemistry and Bioenergetics; vol. 35; pp. 63-69; Nov. 1994.

Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).

Pilla; Electrochemical information and energy transfer in vivo; Proc. 7th IECEC;Washington, D.C.; American Chemical Society; pp. 761-764; (year of publication is sufficiently earlier than the effective U.S. filing date and any foreign priority date) 1972.

Pilla; Electrochemical information transfer at living cell membrane; Ann. N.Y.Acad. Sci.; vol. 238; p. 149-170; Oct. 1974.

Pilla et al.; Electromagnetic fields as first messenger in biological signaling: application to calmodulin-dependent signaling in tissue repair; Biochim. Biophys. Acta; 1810; pp. 1236-1245; Dec. 31, 2011.

Pilla; Electromagnetic fields instantaneously modulate nitric oxide signaling in challenged biological systems; Biochem. Biophys. Res. Commun.; 426(3); pp. 330-333; Sep. 28, 2012.

Pilla; Low-intensity electromagnetic and mechanical modulation of bone growth and repair: are they equivalent?; Journal of Orthopedic Science; vol. 7(3); pp. 420-428; (year of pub. sufficiently earlier than effective US filing date and any foreign priority date) 2002.

Pilla; State of the art in electromagnetic therapeutics: soft tissue applications; Electricity and Magnetism in Biology and Medicine; Bersani (ed.); Kluwer Academic/Plenum Publishers; pp. 871-874; (year of pub. sufficiently earlier than effective US filing date and any foreign priority date) 1999.

Pilla; Weak time-varying and static magnetic fields: from Mechanisms to therapeutic applications; Biological Effects of Electro Magnetic Fields; P. Stavroulakis, ed. Springer Verlag; pp. 34-75; (year of pub. sufficiently earlier than effective US filing date and any foreign priority date) 2003.

Pineros et al.; Calcium channels in higher plant cells: Selectivity, regulation, and pharmacology; J Exp Bot; vol. 48; special issue; pp. 551-577; Mar. 1997.

Pirozzoli et al.; Effects of 50 Hz electromagnetic field exposure on apoptosis and differentiation in a neuroblastoma cell line. Bioelectromagnetics 24, 510-6 (Oct. 2003).

Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.

Rasouli et al.; Attenuation of interleukin-1 beta by pulsed electromagnetic fields after traumatic brain injury; Neurosci. Let.; 519(1); pp. 4-8; Jun. 21, 2012.

Rawe et al.; Control of postoperative pain with a wearable continuously operating pulsed radiofrequency energy device: a preliminary study; Aesthet. Plast. Surg.; 36(2); pp. 458-463; Apr. 1, 2012.

Reale et al.; Modulation of MCP-1 and iNOS by 50-Hz sinusoidal electromagnetic field. Nitric Oxide 15, 50-7 (Aug. 2006).

Ren et al.; Role of interleukin-1? during pain and inflammation (Author Manuscript). Brain Res Rev 60, 57-64 (Apr. 2009).

Rich et al.; Chronic caloric restriction reduces tissue damage and improves spatial memory in a rat model of traumatic brain injury. J Neurosci Res 88, 2933-9 (Oct. 2010).

Rogers et al.; Behavioral and functional analysis of mouse phenotype: SHRIPA, a proposed protocol for comprehensive phenotype assessment. Mamm Genome 8, 711-3 (Oct. 1997).

Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (1-10) (Jun. 2010).

Rohde et al.; PEMF therapy rapidly reduces post-operative pain in TRAM flap patients; Plast. Reconstr. Surg.; 130(5S-1); pp. 91-92; Nov. 1, 2012.

Roland et al.; Effects of pulsed magnetic energy on a microsurgically transferred vessel; Plast. Reconstr. Surg.; 105(4); pp. 1371-1374; Apr. 2000.

Ross et al.; Effect of pulsed electromagnetic field on inflammatory pathway markers in RAW 264.7 murine macrophages; J. Inflamm. Res.; 6; pp. 45-51; Mar. 11, 2013.

Ryaby et al.; The role of insulin-like growth factor in magnetic field regulation of bone formation. Bioelectrochem. Bioenergetics; vol. 35(1-2); pp. 87-91; Nov. 1994.

Sagan, L.; Epidemiological and laboratory studies of power frequency electric and magnetic fields; JAMA; vol. 268(5); pp. 625-629; Aug. 5, 1992.

Saljo et al.; Exposure to short-lasting impulse noise causes microglial and astroglial cell activation in the adult rat brain. Pathophysiology 8, 105-111 (Dec. 2001).

Saljo et al.; Low-level blast raises intracranial pressure and impairs cognitive function in rats: prophylaxis with processed cereal feed. J Neurotrauma 27, 383-9 (Feb. 2010).

Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).

Sandyk, R.; Treatment with AC pulsed electromagnetic fields improves olfactory function in Parkinson's disease. Int J Neurosci 97, 225-33 (Apr. 1999).

Sapolsky; Glucocorticoid toxicity in the hippocampus: temporal aspects of neuronal vulnerability. Brain Res 359, 300-5 (Dec. 16, 1985).

Sarimov, et al.; Exposure to ELF Magnetic Field Tuned to Zn Inhibits Growth of Cancer Cells. Bioelectromagnetics; vol. 26; No. 8; pp. 631-638; Dec. 2005.

Sauerland et al.; Risks and benefits of preoperative high dose methylprednisolone in surgical patients: a systematic review. Drug Saf 23, 449-61 (Nov. 2000).

Schmued et al.; Fluoro-Jade: a novel fluorochrome for the sensitive and reliable histochemical localization of neuronal degeneration. Brain Res 751, 37-46 (Mar. 1997).

Seegers et al.; Activation of signal-transduction mechanisms may underlie the therapeutic effects of an applied electric field. Med Hypotheses 57, 224-30 (Aug. 2001).

Shupak et al.; Human exposure to a specific pulsed magnetic field: effects on thermal sensory and pain thresholds. Neurosci Lett 363, 157-62 (Jun. 10, 2004).

Sisken et al.; Prospects on clinical applications of electrical stimulation for nerve regeneration. J Cell Biochem 52, 404-409 (Apr. 1993).

Sisken, et al.; Static magnetic fields and nerve regeneration (presentation abstract); Bioelectromagnetics Society; 21st Ann Meeting, Long Beach, Jun. 20-24, 1999.

Slepko et al.; Progressive activation of adult microglial cells in vitro. Glia 16, 241-46 (Mar. 1996).

Smith, S.; Calcium cyclotron resonance and diatom mobility; Bioelectromagnetics; vol. 8; pp. 215-227; (year of publication is sufficiently earlier than the effective U.S. filing date and any foreign priority date) 1987.

Stahel et al.; The role of the complement system in traumatic brain injury. Brain Res Brain Res Rev 27, 243-56 (Jul. 1998).

Steinberg et al.; Osteonecrosis of the Femoral Head. Results of core decompression and grafting with and without electrical stimulation. Clin Orthop, 199-208 (Dec. 1989).

Strauch et al; Evidence-based use of pulsed electromagentic field therapy in clinical plastic surgery; Aesthetic Surg. J.; 29(2); pp. 135-143; Mar.-Apr. 2009.

(56) References Cited

OTHER PUBLICATIONS

Teleman et al.; Kinetics of Ca2+ binding to calmodulin and its tryptic fragments studied by 43Ca-NMR. Biochim Biophys Acta 873, 204-13 (Sep. 1986).
Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).
Tepper et al.; Electromagnetic fields increase in vitro and in vivo angiogenesis through endothelial release of FGF-2; FASEB J.; 18(11); pp. 1231-1233; Aug. 2004.
Terpolilli et al.; The novel nitric oxide synthase inhibitor 4-amino-tetrahydro-L-biopterine prevents brain edema formation and intracranial hypertension following traumatic brain injury in mice. J Neurotrauma 26, 1963-75 (Nov. 2009).
Thurman et al.; The epidemiology of sports-related traumatic brain injuries in the United States: recent developments. J Head Trauma Rehabil 13, 1-8 (Apr. 1998).
Trillo et al.; Magnetic fields at resonant conditions for the hydrogen ion affect neurite outgrowth in PC-12 cells: a test of the ion parametric resonance model. Bioelectromagnetics 17, 10-20 (year of publication is sufficiently earlier than the effective U.S. filing date and any foreign priority date) (1996).
Unterberg et al.; Edema and brain trauma. Neuroscience 129(4), 1021-9 (year of publication is sufficiently earlier than the effective U.S. filing date and any foreign priority date) (2004).
Valbona, et al.; Response of pain to static magnetic fields in post-polio patients: A doubleblind pilot study; Arch. Phys. Med. Rehabil.; vol. 78(11); pp. 1200-1203; Nov. 1997.
Vianale et al.; Extremely low frequency electromagnetic field enhances human keratinocyte cell growth and decreases proinflammatory chemokine production. Br J Dermatol 158(6), 1189-96 (Jun. 2008).
Weaver, et al.; The response of living cells to very weak electric fields: The thermal noise limit; Science; vol. 247, No. 4941; pp. 459-462; Jan. 1990.
Weber et al.; Pulsed magnetic fields applied to a transferred arterial loop support the rat groin composite flap; Plast. Reconstr. Surg.; 114(5); pp. 1185-1189; Oct. 2004.
Weinstein, et al.; Ca2+-Binding and Structural Dynamics in the functions of Calmodulin; Ann. Rev. Physiol; vol. 56; pp. 213-236; Mar. 1994.
Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.
Weissman et al.; Activation and inactivation of neuronal nitric oxide synthase: characterization of Ca(2+)-dependent [125I]Calmodulin binding. Eur J Pharmacol 435, 9-18 (Jan. 2002).
Wenk, G.; The nucleus basalis magnocellularis cholinergic system: one hundred years of progress; Neurobiology of Learning and Memory; 67(2); 85-95 (Mar. 1997).
Werner et al.; Regulation of wound healing by growth factors and cytokines; Physiol. Rev.; 83(3); pp. 835-870; Jul. 2003.
Wikipedia; ISM band; 6 pages; retrieved Nov. 30, 2015 from the internet; ( https://en.wikipedia.org/w/index.php?title=ISM_band &oldid=690024749).
Williams et al.; Characterization of a new rat model of penetrating ballistic brain injury. J Neurotrauma 22, 313-31 (Feb. 2005).
World Health Organization; Neurlogical disorders: publiic health challenges; © 2006; 231 pages; retrieved Oct. 26, 2015 from the internet; http://www.who.int/mental_health/neurology/neurological_disorders_report_web.pdf.
Xuan et al.; Transcranial low-level laser therapy improves neurological performance in traumatic brain injury in mice: effect of treatment repetition regimen; Plos One; 8(1); p. e53454; 9 pages; Jan. 7, 2013.
Yasuda, I.; Part III. Clinical Studies: Mechanical and electrical callus; Annals of the New York Academy of Sciences; vol. 238; pp. 457-465 (Oct. 1974).
Yu et al.; Effects of 60 Hz electric and magnetic fields on maturation of the rat neopallium. Bioelectromagnetics 14, 449-58 (year of publication is sufficiently earlier than the effective U.S. filing date and any foreign priority date) (1993).
Yumoto, et al.; Coordination Structures of Ca2+ and Mg2+ in Akazara Scallop Troponin C in Solution; Eur. J. Biochem; vol. 268(23); pp. 6284-6290; Dec. 2001.
Yurdagul et al.; Altered nitric oxide production mediates-specific PAK2 and NF-kB activation by flow; Mol. Biol. Cell.; 24(3); pp. 398-408; Feb. 2013.
Zaloshnja et al.; Prevalence of long-term disability from traumatic brain injury in the civilian population of the United States, 2005. J Head Trauma Rehabil 23, 394-400 (Nov./Dec. 2008).
Zdeblick; A prospective, randomized study of lumbar fusion: preliminary results; Spine; vol. 18; pp. 983-991; Jun. 15, 1993.
Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.
Zhadin, et al.; Ion Cyclotron Resonance in Biomolecules; Biomed Sci; vol. 1; pp. 245-250; (year of publication is sufficiently earlier than the effective U.S. filing date and any foreign priority date) 1990.
Zhadin, M.; Combined action of static and alternating magnetic fields on ion motion in a macromolecule; Theoretical aspects; Bioelectromagnetics; vol. 19(5); pp. 279-292; (year of pub. sufficiently earlier than effective US filing date and any foreign priority date) 1998.
Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; Aug. 18, 1997.
Ziebell et al.; Involvement of pro- and anti-inflammatory cytokines and chemokines in the pathophysiology of traumatic brain injury. Neurotherapeutics 7, 22-30 (Jan. 2010).
Zizic et al.; The treatment of osteoarthritis of the knee with pulsed electrical stimulation. J Rheumatol 22, 1757-61 (Sep. 1995).
Pilla et al.; U.S. Appl. No. 14/171,613 entitled "Apparatus and method for electromagnetic treatment of neurodegenerative conditions," filed Feb. 3, 2014.

* cited by examiner

PEMF: Enhances CaM activation (millisec, real-time);

$Ca^{2+}$ + CaM ⇌ $Ca^{2+}$CaM (*kinetic asymmetry*)

Increases enzyme activity (millisec, real-time);

$Ca^{2+}$CaM + cNOS ⟶ NO (signaling)

Modulates inflammation and repair

NO ⟶ cGMP ⟶ Cytokines, Growth Factors

PEMF Accelerates PDE inhibition of cGMP (real-time)

$Ca^{2+}$CaM + PDE + cGMP ⟶ GMP

FIG. 1A

METHOD AND APPARATUS FOR ELECTROMAGNETIC TREATMENT OF LIVING SYSTEMS

CROSS REFERENCE TO RELATED APPLICATIONS

This application claims priority to U.S. provisional patent application No. 62/075,122, filed on Nov. 4, 2014, and titled "METHOD AND APPARATUS FOR ELECTROMAGNETIC TREATMENT OF LIVING SYSTEMS," the entirety of which is herein incorporated by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The disclosure relates generally to the field of therapeutic devices and methods for treating patients.

BACKGROUND

Described herein are electromagnetic treatment devices, systems and methods. Some embodiments pertain generally to a method and apparatus for therapeutic and prophylactic treatment of animal and human cells and tissues. In particular, some embodiments pertain to use of non-thermal time-varying electromagnetic fields configured to accelerate the asymmetrical kinetics of the binding of intracellular ions to their respective binding proteins which regulate the biochemical signaling pathways living systems employ to reduce the inflammatory response to injury, and to enhance healing and well-being. Other embodiments pertain to the non-thermal application of repetitive pulse bursts of sinusoidal, rectangular, chaotic or arbitrary waveform electromagnetic fields to instantaneously accelerate ion-buffer binding in signaling pathways in animal and human cells and tissues using ultra lightweight portable coupling devices such as inductors and electrodes, driven by miniature signal generator circuitry that can be incorporated into an anatomical positioning device such as a dressing, bandage, compression bandage, compression dressing; lumbar or cervical back, shoulder, head, neck and other body portion wraps and supports; garments, hats, caps, helmets, mattress pads, seat cushions, beds, stretchers, and other body supports in cars, motorcycles, buses, trains, airplanes, boats, ships and the like.

In some embodiments, the proposed EMF transduction pathway relevant to tissue maintenance, repair and regeneration, begins with voltage-dependent Ca2+ binding to CaM, which is favored when cytosolic Ca2+ homeostasis is disrupted by chemical and/or physical insults at the cellular level. Ca/CaM binding produces activated CaM that binds to, and activates, cNOS, which catalyzes the synthesis of the signaling molecule NO from L-arginine. This pathway is shown in its simplest schematic form in FIG. 1A. FIG. 1A is a schematic summary of the body's primary anti-inflammatory cascade and the proposed manner by which PEMF may accelerate postoperative pain relief. Surgical injury increases cytosolic Ca2+, which activates CaM. PEMF accelerates CaM activation thereby enhancing NO/cGMP anti-inflammatory signaling. PEMF also enhances CaM-dependent PDE activation, which accelerates cGMP inhibition. PEMF dosing must take into account the competing dynamics of NO/cGMP signaling and PDE inhibition of cGMP.

As shown in FIG. 1A, cNOS* represents activated constitutive nitric oxide synthase (cNOS), which catalyzes the production of NO from L-arginine, which, in turn, activates soluble gyanylyl cyclase, sGC. The term "sGC*" refers to activated guanylyl cyclase which catalyzes cyclic guanosine monophosphate (cGMP) formation when NO signaling modulates the tissue repair pathway. "AC*" refers to activated adenylyl cyclase, which catalyzes cyclic adenosine monophosphate (cAMP) when NO signaling modulates differentiation and survival.

According to some embodiments, an EMF signal can be configured to accelerate cytosolic ion binding to a cytosolic buffer, such as voltage dependent Ca2+ binding to CaM, because the rate constant for binding, kon is much greater than the rate constant for unbinding, koff, imparting rectifier-like properties to ion-buffer binding, such as Ca2+ binding to CaM.

Yet another embodiment pertains to application of sinusoidal, rectangular, chaotic or arbitrary waveform electromagnetic signals, having frequency components below about 100 GHz, configured to accelerate the binding of intracellular Ca2+ to a buffer, such as CaM, to enhance biochemical signaling pathways in animal and human cells and tissues. Signals configured according to additional embodiments produce a net increase in a bound ion, such as Ca2+, at CaM binding sites because the asymmetrical kinetics of Ca/CaM binding allows such signals to accumulate voltage induced at the ion binding site, thereby accelerating voltage-dependent ion binding. Examples of therapeutic and prophylactic applications are modulation of biochemical signaling in anti-inflammatory pathways, modulation of biochemical signaling in cytokine release pathways, modulation of biochemical signaling in growth factor release pathways; edema and lymph reduction, anti-inflammatory, post-surgical and post-operative pain and edema relief, nerve, bone and organ pain relief, increased local blood flow, microvascular blood perfusion, treatment of tissue and organ ischemia, brain tissue ischemia from stroke or traumatic brain injury, treatment of neurological injury and neurodegenerative diseases such as Alzheimer's and Parkinson's; angiogenesis, neovascularization; enhanced immune response; enhanced effectiveness of pharmacological agents; nerve regeneration; prevention of apoptosis; modulation of heat shock proteins for prophylaxis and response to injury or pathology.

In some variations the systems, devices and/or methods generally relate to application of electromagnetic fields (EMF), and in particular, pulsed electromagnetic fields (PEMF), including a subset of PEMF in a radio frequency domain (e.g., pulsed radio frequency or PRF), for the treatment of any of the applications disclosed herein in animals and humans, including pain, edema, tissue repair and head, cerebral and neural injury, and neurodegenerative conditions.

Transient elevations in cytosolic Ca2+, from external stimuli as simple as changes in temperature and receptor activation, or as complex as mechanical disruption of tissue, will activate CaM. Once Ca2+ ions are bound, a conformational change will allow CaM bind to and activate a number of key enzymes involved in cell viability and function, such as the endothelial and neuronal constitutive nitric oxide synthases (cNOS); eNOS and nNOS, respectively. As a consequence, NO is rapidly produced, albeit in lower concentrations than the explosive increases in NO produced by inducible NOS (iNOS), during the inflammatory response. In contrast, these smaller, transient increases in NO produced by Ca/CaM-binding will activate soluble guanylyl cyclase (sGC), which will catalyze the formation of cyclic guanosine monophosphate (cGMP). The CaM/NO/cGMP signaling pathway can rapidly modulate blood flow in response to normal physiologic demands, as well as to inflammation. Importantly, this same pathway will also rapidly attenuate expression of cytokines such as interleukin-1beta (IL-1β), and iNOS and stimulate anti-apoptotic pathways in neurons. All of these effects are mediated by calcium and cyclic nucleotides, which in turn regulate growth factors such as basic fibroblast growth factor (FGF-2) and vascular endothelial growth factor (VEGF), resulting in pleiotrophic effects on cells involved in tissue repair and maintenance. PEMF can also accelerate the inhibition of cGMP by phosphodiesterase (PDE) Improved PEMF signal configurations and treatment regimens are disclosed herein that can minimize the inhibition of cGMP by PDE.

Therefore, a need exists for an apparatus and a method that modulates the biochemical pathways that regulate animal and human tissue response to maximize the rate of cGMP production while minimizing the rate of inhibition of cGMP. In some embodiments, an apparatus incorporates miniaturized circuitry and light weight coil applicators or electrodes to deliver any of the waveforms described herein thus allowing the apparatus to be low cost, portable and, if desired, disposable.

SUMMARY OF THE DISCLOSURE

The present invention relates to methods and apparatuses for treating patients with pulsed electromagnetic therapies (PEMF). The PEMF waveform and the period between PEMF waveform pulses can be configured to simultaneously increase the rate of cGMP production and to minimize the rate of inhibition of cGMP by compounds such as PDE.

In particular, described herein are methods of optimizing PEMF treatment based on the surprising finding that the effectiveness of a non-invasive, relatively low-energy or very low-energy PEMF treatment depends on the ratio of the duration of the treatment interval and the duration of the inter-treatment interval (also referred to herein as the inter-treatment period). The methods described herein are invented from the new finding that the for externally-applied low-energy or (in some variations) very low-energy PEMF treatments, a ratio of treatment interval to inter-treatment period of greater than about 1:6 (e.g., an inter-treatment period that is greater than six times the treatment interval) results in efficacious treatment, whereas ratios less than 1:6 do not. In addition, in some variations it may be beneficial to have ratios of treatment interval to inter-treatment period of less than about 1:100. For example, the ratio of treatment interval to inter-treatment period may be greater than about 1:7, greater than about 1:8, greater than about 1:9, greater than about 1:10, greater than about 1:11, greater than about 1:12, greater than about 1:15, greater than about 1:18, etc., and/or between about 1:6 and 1:1000, between about 1:6 and 1:500, between about 1:6 and 1:100, between about 1:6 and 1:75, between about 1:6 and 1:50, between about 1:8 and 1:1000, between about 1:8 and 1:500, between about 1:8 and 1:100, etc.

The apparatuses described herein may be generally configured to be worn against the body (e.g., incorporated into a garment, jewelry, hat, bed, chair, etc.), and may be specifically adapted/configured to deliver non-invasive, relatively low-energy or very low-energy PEMF treatment in which the ratio of treatment interval to inter-treatment period is as described herein.

For example described herein are methods for treating a patient (e.g., human, animal, etc.) that may generally include: generating a pulsed electromagnetic field (PEMF) from a pulsed electromagnetic field source; applying the pulsed electromagnetic field in proximity to a target region affected by an injury or condition to reduce a physiological response to the injury or condition for a treatment interval that is greater than 10 minutes; discontinuing the application of the pulsed electromagnetic field for an inter-treatment period that is greater than six times the treatment interval; and repeating, for a plurality of times, the steps of generating, applying and discontinuing.

A pulsed electromagnetic field source may include any apparatus, including those described herein or otherwise known in the art, that can be used to apply relatively low-energy PEMF signals. Examples of such devices and PEMF signals (including low-energy PEMF signals) are described, for example, in U.S. patent applications: U.S. Pat. Nos. 7,744,524, 7,740,574, 8,415,123, 7,758,490, 7,896,797 and 8,343,027, and pending applications no.: US-2010-0210893, US-2010-0222631, US-2013-0274540, US-2014-0046115, US-2014-0046117, US-2011-0207989, US-2012-0116149, US-2014-0213843, US-2014-0213844, and US-2012-0089201-A1. Each of these patents and pending applications is herein incorporated by reference in its entirety, and in particular for its teaching of PEMF application devices, waveforms, and therapies.

A relatively low-energy PEMF waveform may generally apply milliTesla (mT), e.g., between about 1 and 100 mT, magenitc field strength, or average magnetic field strength. Very low-energy PEMF may apply microTesla (µT), e.g., less than 1 mT, less than 100 µT, less than 50 µT, less than 20 µT, less than 10 µT, less than 5 µT, etc. The PEMF signal, though relatively or very low energy may be applied in the specific pulsed waveforms as described herein to any target region.

A target region may be any body region, including surface (e.g., skin) or internal (e.g., brain, organ, etc.) region, particularly those that are more superficially located. Wounds such as surgical wounds are an example of a target region. Nerves, including spinal, peripheral or central (e.g., brain) nervous system regions may also be treated as described herein. The treatments described herein may be used to treat a medical disorder, and may modulate or improve a physiological response to the injury or condition, including but not limited to, swelling/inflammation, necrosis, healing (e.g., tissue growth, cell migration), scarring, etc.

In general, a treatment interval may include the period during which treatment (PEMF energy) is actively being applied, for example, as a burst or plurality of bursts of pulses. The waveforms may be applied at a regular, irregular or random duration, period or wave-shape within the burst (envelope) and the amplitude of the envelope may be regular (e.g., sinusoidal, square, etc.), irregular, or random. In particular, sinusoidal pulses at a carrier frequency (e.g., of 27.12 or a harmonic thereof) may be applied within a rectangular envelope that had a burst duration (e.g., greater than 200 microseconds, greater than 300 microseconds, greater than 400 microseconds, greater than 500 microseconds, greater than 600 microseconds, between 500 microseconds and 1 second, etc.), and may be repeated at a burst repetition rate. The treatment interval may therefore include quiescent periods, but they are typically part of the inter-pulse or inter-burst periods defining the periodicity of the waveforms or burst of waveforms. A treatment interval may be between 5 and 600 minutes, but more likely between 5 and 50 minutes. As described herein, it may be particularly efficacious to apply treatment for a treatment interval of greater than about 10 minutes, e.g., greater than about 11, 12, 13, 14, 15, 16, 17, 18, 19, 20, etc. minutes.

During any of the treatments described herein the treatment periods may be divided by off-times (inter-treatment periods) during which no PEMF signals are applied by the apparatus, which may be particularly configured to prevent the application of any PEMF signal during this inter-treatment period.

The method of claim 1, wherein the pulsed electromagnetic field is configured to simultaneously increase the rate of ion-dependent signaling and to minimize the rate of inhibition of such signaling by natural compounds. This period may be referred to as a period during which the PEMF signal application is discontinued, e.g., discontinuing the application of the pulsed electromagnetic field for an inter-treatment period (or "off time"). Following the discontinuation, another treatment period (and another inter-treatment period, off-time) may be repeated. The waveforms applied during the subsequent treatment periods may be the same or different. For example, the waveform characteristics, such as amplitude, frequency (e.g. burst frequency and/or pulse frequency and/or carrier wave frequency), duration (burst duration, pulse duration), and/or waveform and/or envelope (burst) shape, may be different between, or in some variations within, subsequent treatment periods. The duration of the subsequent treatment period may be the same or different, though they may still be greater than some minimum treatment period duration (e.g., greater than 10 min, 11 min, 12 min, 13 min, 14 min, 15 min, 20 min, 25 min, 30 min, 40 min, 50 min, 60 min, etc.) and/or less than a maximum treatment period duration (e.g., less than 50 min, 60 min, 70 min, 80 min, 90 min, 2 hrs, 2.5 hrs, 3 hrs, etc.), where the minimum is always less than the maximum. In some variations, the method or apparatus may adjust one or more characteristics of the treatment period and/or the treatment period duration based on feedback measured or otherwise received from the patient, including feedback based on a detected level of a biomarker.

The pulsed electromagnetic field may be configured to simultaneously increase the rate of cGMP signaling and to minimize the rate of inhibition of such signaling by compounds such as phosphodiesterase (PDE). The pulsed electromagnetic field may be configured to simultaneously increase the rate of cGMP signaling and to minimize the rate of inhibition of such signaling by compounds such as phosphodiesterase (PDE), is applied for a duration consistent with the above.

The application treatment may include any appropriate number of repetitions, and may be opend-ended (e.g., stopped manually by the patient and/or a medical professional). For example repeating may comprise repeating for at least 10 times, 11 times, 12 times, 20 times, 30 times, 40 times, 50 times, etc. or for some minimum time interval (e.g., 20 min, 25 min, 30 min, 35 min, 40 min, 50 min, 60 min, 90 min, 2 hrs, 4 hrs, 8 hrs, 12 hrs, 18 hrs, 24 hrs, 36 hrs, 2 days, 3 days, 4 days, 5 days, 7 days, 14 days, etc.).

As mentioned, the pulsed electromagnetic field may consist of a burst having any appropriate relatively or very low PEMF waveform characteristics. For example, the PEMF signal within a treatment period may have a duration of greater than 2 msec of a 27.12 MHz carrier repeating at between 1 and 20 bursts/sec at an amplitude of between 2 and 10 µT. The pulsed electromagnetic field may include a burst having a duration of between 2 and 10 msec of a carrier wave repeating at between 1 and 10 bursts/sec at an amplitude of between 3 and 8 µT.

The length of the first treatment interval and the length of the inter-treatment period are selected to minimize phosphodiesterase (PDE) production in the patient.

Any of these methods may also include monitoring the physiological response; and modifying the pulsed electromagnetic field in response to the monitoring step. For example, they may include monitoring the physiological response; and discontinuing treatment once an acceptable level of the physiological response is reached.

The methods may also include modulating inflammatory cytokines and growth factors at the target region by applying the pulsed electromagnetic field to simultaneously increase the rate of such modulation and to minimize the rate of inhibition of such modulation by natural compounds. These methods may also include accelerating the healing of the target region by applying the pulsed electromagnetic field to simultaneously increase the rate of healing and to minimize the rate of inhibition of such healing.

Applying may include applying the pulsed electromagnetic field in proximity to a target region affected by a neurological injury or condition to reduce a physiological response comprises reducing a concentration of IL-1β.

As mentioned above, these methods may be used to treat any appropriate injury or condition, including a neurodegenerative disease, e.g., Parkinson's disease. Alzheimer's disease, etc. The injury or condition may be a traumatic brain injury (TBI). The injury or condition may be a post-operative inflammation and pain.

Also described herein are apparatuses configured to perform any of these methods. For example, an apparatus for applying pulsed electromagnetic field (PEMF) energy to a subject may include: a generator unit including a signal generator configured to generate a PEMF waveform having configured to simultaneously increase the rate of ion-dependent signaling and to minimize the rate of inhibition of such signaling; a programmable control unit configured to repeatedly provide a signal to the generator unit corresponding to the PEMF waveform for a treatment interval that is 10 minutes or greater followed immediately by an off time having an inter-treatment period that is greater than six times the treatment interval; and an applicator unit configured to be worn by the subject, wherein the generator unit is configured to power the applicator unit to drive transmission of a PEMF signal from the applicator unit based on the PEMF waveform.

The programmable control unit may be programmed to provide an inter-treatment period that is between six and 100 times the treatment interval. The programmable control unit may be configured to prevent the generation of a pulsed electromagnetic field during the inter-treatment period.

Any of these apparatuses may include a shut off to stop the generator unit during the inter-treatment period.

Any appropriate applicator may be used, particularly flexible loop applicators, which may be bent or shaped, though remain a coil. In some variations, the applicator comprises a first loop configured to provide the PEMF waveform and a second loop configured to provide a second PEMF waveform.

A programmable control unit may be configured to repeatedly provide the same signal to the generator unit corresponding to the PEMF waveform.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a schematic representation of the biological EMF transduction pathway which is a representative target pathway of EMF signals configured according to embodiments described herein.

DETAILED DESCRIPTION

Pulsed electromagnetic fields (PEMF) reduce postoperative pain and narcotic requirements in breast augmentation, reduction, and reconstruction patients. PEMF treatment can also be used to reduce post-operative pain in other surgical procedures. PEMF enhances calmodulin-dependent nitric oxide, which enhances cyclic guanosine monophosphate signaling and phosphodiesterase activity, which blocks cyclic guanosine monophosphate. This invention describes means to configure PEMF dosing to minimize the effect of the competing response of phosphodiesterace activity.

Figure 1B:
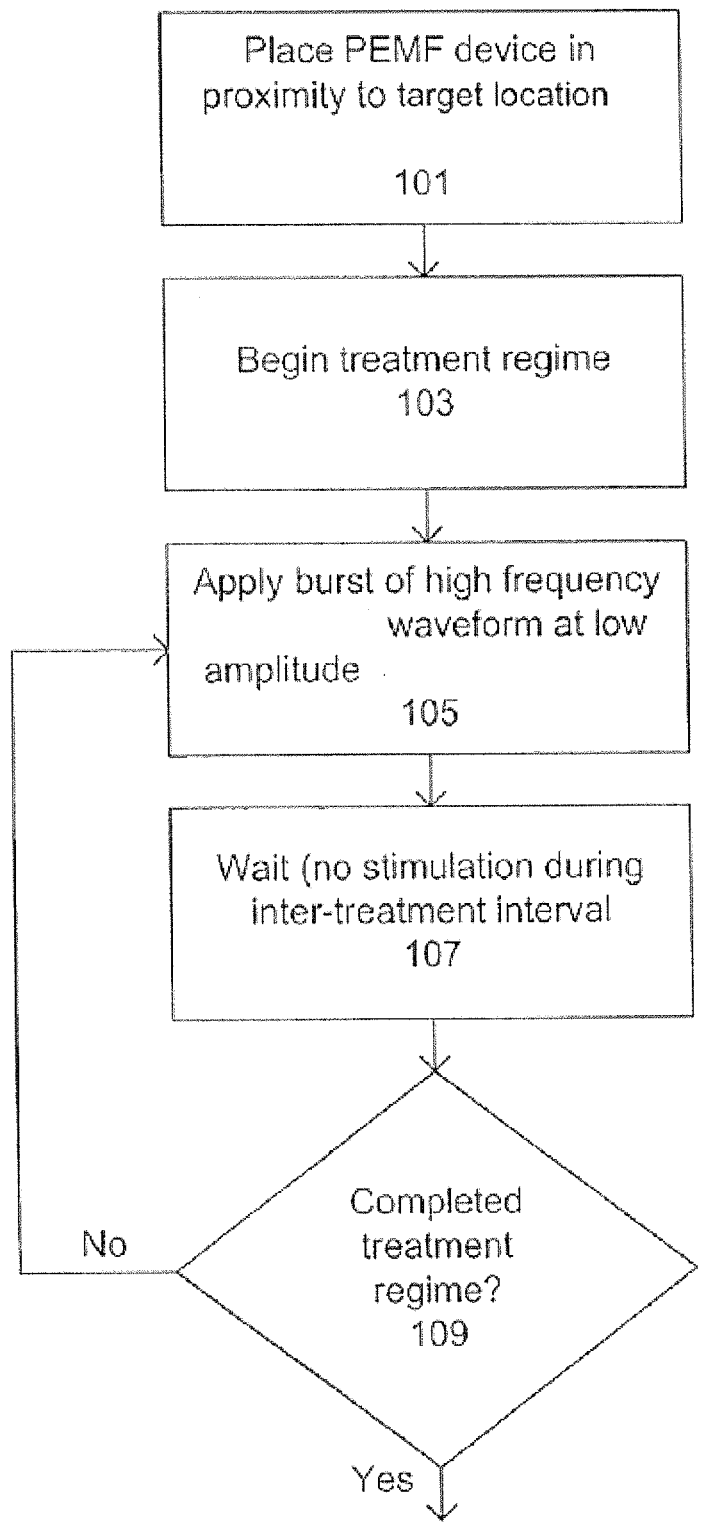
FIG. 1B is a flow diagram of a method for treating a patient according to an embodiment of the devices and methods described herein.

FIG. 1B is a flow diagram of a method for treating a subject with a PEMF. In some variations, before beginning the treatment, one or more (or a range of) waveforms may be determined that target the appropriate pathway for the target tissue. In such embodiments, once this determination is made, electromagnetic fields are applied to the target location.

Figure 2A:
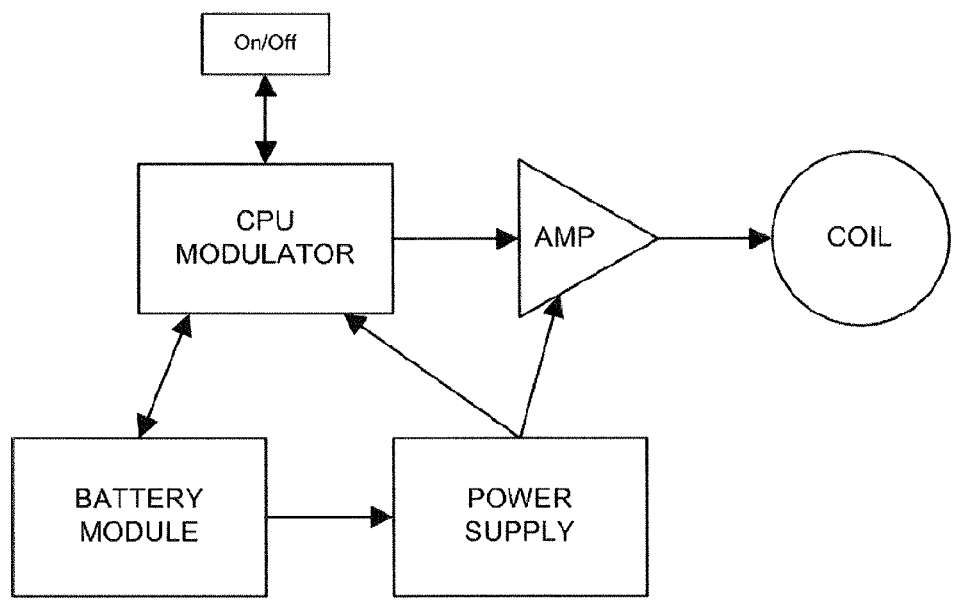
FIG. 2A is a block diagram of miniaturized circuitry for use with a coil applicator according to some embodiments described.

FIG. 2A illustrates a block diagram of an EMF delivery apparatus as described according to some embodiments. As shown in FIG. 2A, the apparatus may have miniaturized circuitry for use with a coil applicator. In some embodiments, the apparatus may include a CPU MODULATOR, a BATTERY MODULE, a POWER SUPPLY, On/Off switch, and an output amplifier, AMP, as illustrated. In further variations, the CPU MODULATOR may be an 8 bit 4 MHz micro-controller; however, other suitable bit-MHz combination micro-controllers may be used as well. For example, in some embodiments, the CPU MODULATOR may be programmed for a given carrier frequency or pulse duration, such as about 27.12 MHz sinusoidal wave. Moreover, the CPU MODULATOR may be programmed for a given burst duration, for example about 3 msec. In further variations, the CPU MODULATOR may be programmed to provide a given in situ peak electric field, for example 20 V/m; or a given treatment time, for example about 15 minutes; and/or a given treatment regimen, for example about 10 minutes about every hour. The CPU MODULATOR may also be programmed to deliver an EMF waveform to the target ion binding pathway.

Figure 2B:
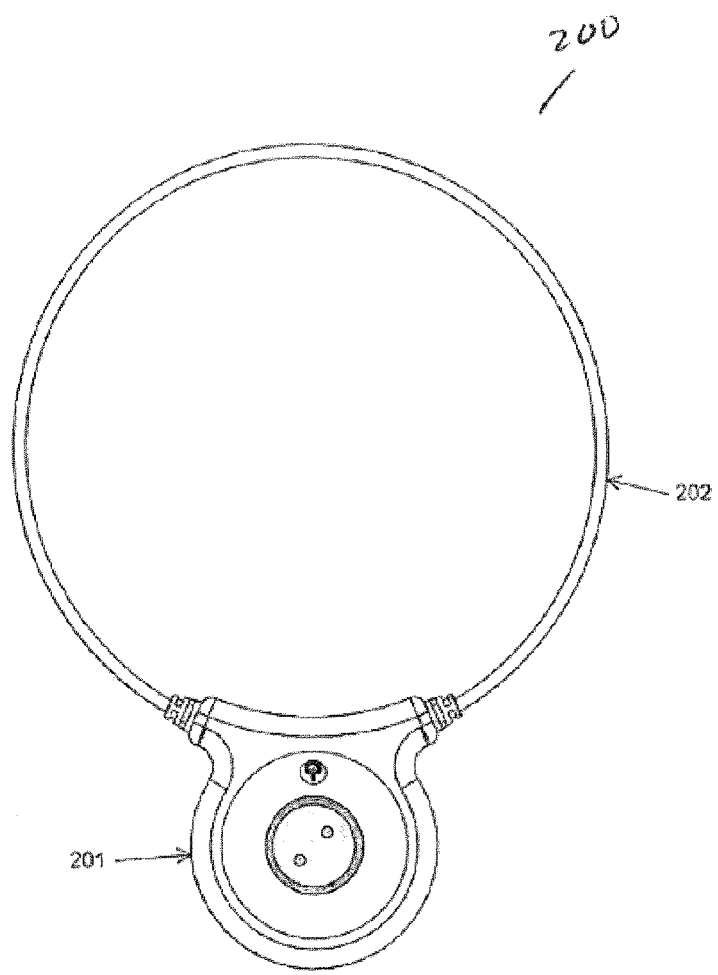
FIG. 2B illustrates a device for application of electromagnetic signals according to an embodiment of the devices and methods described herein.

Some embodiments combine the signal generation and coil or electrode applicator into one portable or disposable unit, such as illustrated in FIG. 2B (which will be described in greater detail below) for the case of an inductively coupled signal. In some variations, when electrical coils are used as the applicator, the electrical coils can be powered with a time varying magnetic field that induces a time varying electric field in a target pathway structure according to Faraday's law. An electromagnetic field generated by a circuit such as shown in FIG. 2A can also be applied using electrochemical coupling, wherein electrodes are in direct contact with skin or another outer electrochemically conductive boundary of a target pathway structure.

In yet another embodiment, the electromagnetic field generated by the generating circuit of FIG. 2A (or FIG. 2B) can also be applied using electrostatic coupling wherein an air gap exists between a generating device such as an electrode and a target pathway structure such as a molecule, cell, tissue, and organ of a plant animal or human. Advantageously, the ultra lightweight coils and miniaturized circuitry, according to some embodiments, allow for use with common physical therapy treatment modalities and at any location on a plant, animal or human for which any therapeutic or prophylactic effect is desired. An advantageous result of application of some embodiments described is that a living organism's wellbeing can be maintained and enhanced.

Figure 2C:
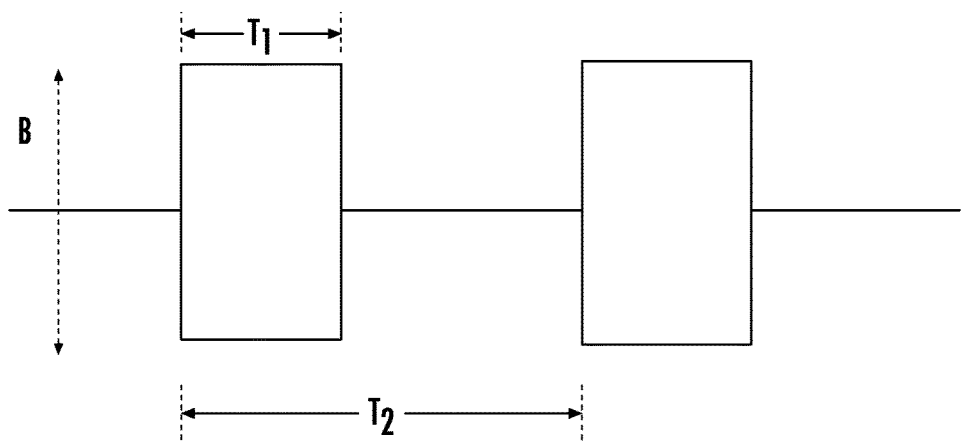
FIG. 2C illustrates a waveform delivered to a target pathway structure of a plant, animal or human, such as a molecule cell, tissue, organ, or partial or entire organism, according to some embodiments described.
Figure 3:
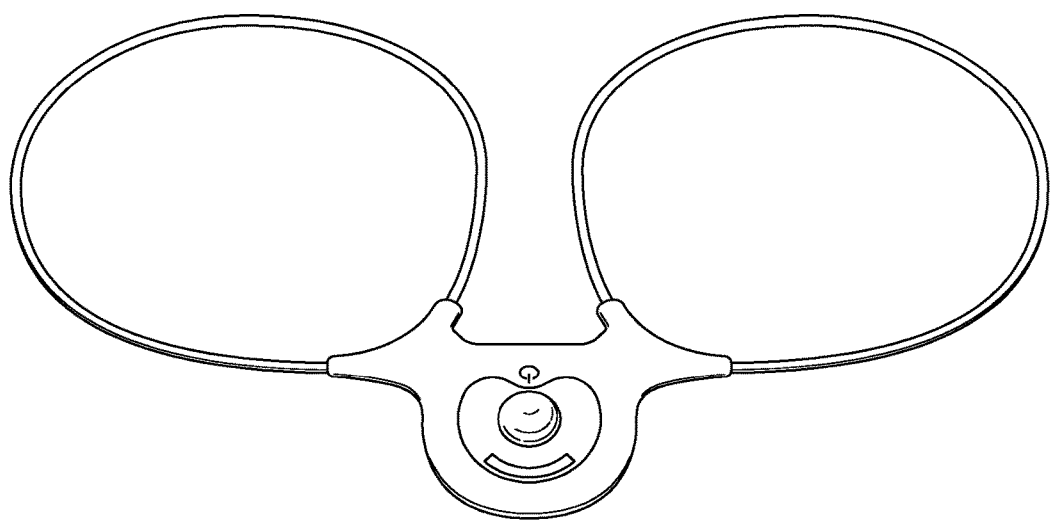
FIG. 3 is a photograph illustrating a disposable dual coil PEMF device used in some of the embodiments described herein. The disposable dual coil PEMF includes a battery-powered signal generator is at the bottom between the coils. A nonthermal pulse-modulated radio frequency PEMF signal, configured to modulate NO signaling, may be delivered to tissue with a preprogrammed dosing regimen for each cohort.

Referring to FIG. 2C, an embodiment according to the present invention of an induced electric field waveform delivered to a target pathway structure is illustrated. As shown in FIG. 2C, burst duration and period are represented by T1 and T2, respectively. In some embodiments, the signal within the rectangular box designated at T1 can be, rectangular, sinusoidal, chaotic or random, provided that the waveform duration or carrier period is less than one-half of the target ion bound time. The peak induced electric field is related to the peak induced magnetic field, shown as B in FIG. 2C, via Faraday's Law of Induction.

FIG. 2B illustrates an embodiment of an apparatus 200 that may be used. The apparatus is constructed to be self-contained, lightweight, and portable. A circuit control/signal generator 201 may be held within a (optionally wearable) housing and connected to a generating member such as an electrical coil 202. In some embodiments, the circuit control/signal generator 201 is constructed in a manner that given a target pathway within a target tissue, it is possible to choose waveform parameters that satisfy a frequency response of the target pathway within the target tissue. For some embodiments, circuit control/signal generator 201 applies mathematical models or results of such models that approximate the kinetics of ion binding in biochemical pathways. Waveforms configured by the circuit control/signal generator 201 are directed to a generating member 202. In some variations, the generating member 202 comprises electrical coils that are pliable and comfortable. In further embodiments, the generating member 202 is made from one or more turns of electrically conducting wire in a generally circular or oval shape, any other suitable shape. In further variations, the electrical coil is a circular wire applicator with a diameter that allows encircling of a subject's cranium. In some embodiments, the diameter is between approximately 6-8 inches. In general, the size of the coil may be fixed or adjustable and the circuit control/signal generator may be matched to the material and the size of the applicator to provide the desired treatment.

The apparatus 200 may deliver a pulsing magnetic field that can be used to provide treatment. In some embodiments, the device 200 may apply a pulsing magnetic field for a prescribed time and can automatically repeat applying the pulsing magnetic field for as many applications as are needed in a given time period, e.g. 6-12 times a day. The device 200 can be configured to apply pulsing magnetic fields for any time repetition sequence. Without being bound to any theory, it is believed that when electrical coils are used as a generating member 202, the electrical coils can be powered with a time varying magnetic field that induces a biologically and therapeutically effective time varying electric field in a target tissue location.

In other embodiments, an electromagnetic field generated by the generating member 202 can be applied using electrochemical coupling, wherein electrodes are in direct contact with skin or another outer electrically conductive boundary of the target tissue (e.g. skull or scalp). In other variations, the electromagnetic field generated by the generating member 202 can also be applied using electrostatic coupling wherein an air gap exists between a generating member 202 such as an electrode and the target tissue. In further examples, a signal generator and battery is housed in the miniature circuit control/signal generator 201 and the miniature circuit control/signal generator 201 may contain an on/off switch and light indicator. In further embodiments, the activation and control of the treatment device may be done via remote control such as by way of a fob that may be programmed to interact with a specific individual device. In other variations, the treatment device further includes a history feature that records the treatment parameters carried out by the device such that the information is recorded in the device itself and/or can be transmitted to another device such as computer, smart phone, printer, or other medical equipment/device.

In other variations, the treatment device 200 has adjustable dimensions to accommodate fit to a variety of patient sizes and anatomy. For example, the generating member 202 may comprise modular components which can be added or removed by mated attaching members. Alternatively, the treatment device 200 may contain a detachable generating member (e.g. detachable circular coil or other configurations) that can be removed and replaced with configurations that are better suited for the particular patient's needs. A circular coil generating member 202 may be removed and replaced with an elongate generating member such that PEMF treatment can be applied where other medical equipment may obstruct access by a circular generating member 202. In other variations, the generating member may be made from Litz wire that allows the generating member to flex and fold to accommodate different target areas or sizes.

The PEMF devices disclosed herein can be used to treat patients with post-operative pain. Acute postoperative pain is a significant medical problem. Postoperative pain must be managed effectively to optimize surgical outcomes, reduce morbidity, shorten the duration of hospital stay, and control ever-increasing health-care costs [1]. For the vast majority of surgical procedures, pain mechanisms involve increased sensitivity of nociceptors due to increased presence of proinflammatory cytokines in the wound milieu [2]. Narcotics are most commonly used to treat postoperative pain; however, narcotics do not reduce nociceptor sensitivity and cause undesirable side effects and potential addiction. Alternative approaches to decrease post-operative pain involve slowing the appearance of proinflammatory agents at the surgical site [2].

To this end, a new modality, nonthermal, nonpharmacologic radio frequency pulsed electromagnetic field (PEMF) therapy has been reported to instantaneously enhance calmodulin (CaM)-dependent nitric oxide (NO) release in challenged cells and tissues. This, in turn, enhances the body's primary anti-inflammatory pathway, CaM-dependent nitric oxide/cyclic guanosine monophosphate (NO/cGMP) signaling [3e7]. In the surgical context, NO/cGMP signaling decreases the rate of release of proinflammatory cytokines, such as interleukin-1 beta (IL [interleukin]-1b) [8], and increases the release of growth factors, such as fibroblast growth factor-2 (FGF-2) [9], in the wound milieu. This mechanism is schematically represented in FIG. 1A. PEMF modulation of angiogenesis via effects on FGF-2 has been reported [10-15]. In some studies, the PEMF effect could be blocked with an FGF-2 inhibitor, consistent with a PEMF effect on NO/cGMP signaling [12, 13].

In the clinical setting, PEMF has been reported to accelerate postoperative pain decrease, with a concomitant reduction in narcotic requirements, in double-blinded, randomized clinical studies on breast reduction (BR) [16], breast augmentation [17, 18], and autologous flap breast reconstruction [19]. The BR study also showed that PEMF reduced inflammation by reducing IL-1 beta more than two-fold in the wound exudate, which correlated with the higher rate of pain reduction from PEMF [16]. PEMF can and has been used throughout the body, including after abdominoplasties, major intra-abdominal surgery, extremity procedures, and facial fat grafting [20, 21].

Taken together, preclinical and clinical results support an anti-inflammatory mechanism for PEMF based on modulation of CaM-dependent NO/cGMP signaling. However, the NO/cGMP cascade is dynamic [22] and regulated, in part, by phosphodiesterase (PDE) inhibition of cyclic guanosine monophosphate (cGMP) [23]. This inhibition is particularly important for PEMF therapy because PDE isoenzymes are also CaM-dependent, meaning the timing of PDE activity is modulated by the same PEMF signal that modulates the timing of NO/cGMP signaling [24]. Thus, although the dynamics of NO/cGMP signaling in challenged tissue can be modulated by PEMF, the effect of PEMF dosing on the competing dynamics of CaM-dependent NO/cGMP signaling and PDE inhibition of cGMP on pain outcome must be taken into account.

For example, a number of patients with post-operative pain were treated with PEMF and studied. Specifically, two prospective, nonrandomized, active cohorts of breast reduction patients, with 15 min PEMF per 2 h; "Q2 (active)", and 5 min PEMF per 20 min; "5/20 (active)", dosing regimens were added to a double-blind clinical study wherein 20 min PEMF per 4 h, "Q4 (active)", dosing was shown to significantly accelerate postoperative pain reduction compared with Q4 shams. Postoperative visual analog scale pain scores and narcotic use were compared.

Figure 4:
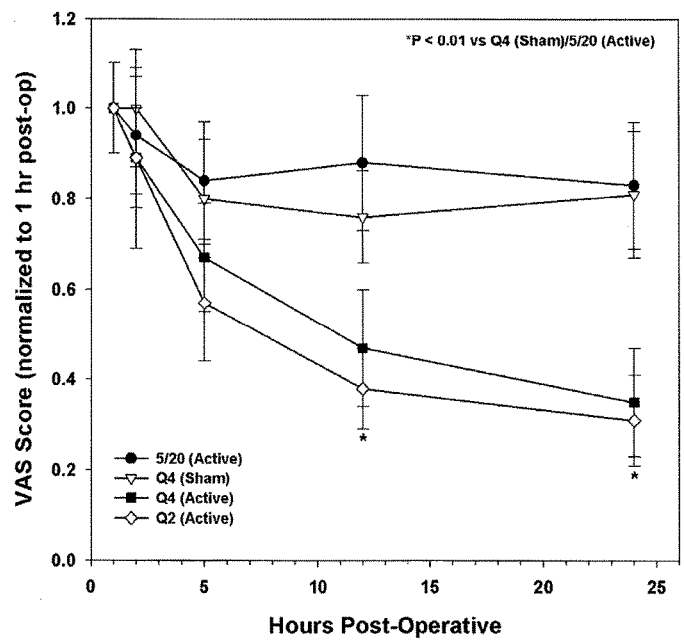
FIG. 4 is a graph showing the effect of different PEMF therapy regimens on the rate of pain reduction following breast reduction surgery in accordance with various embodiments of pain treatments.
Figure 5:
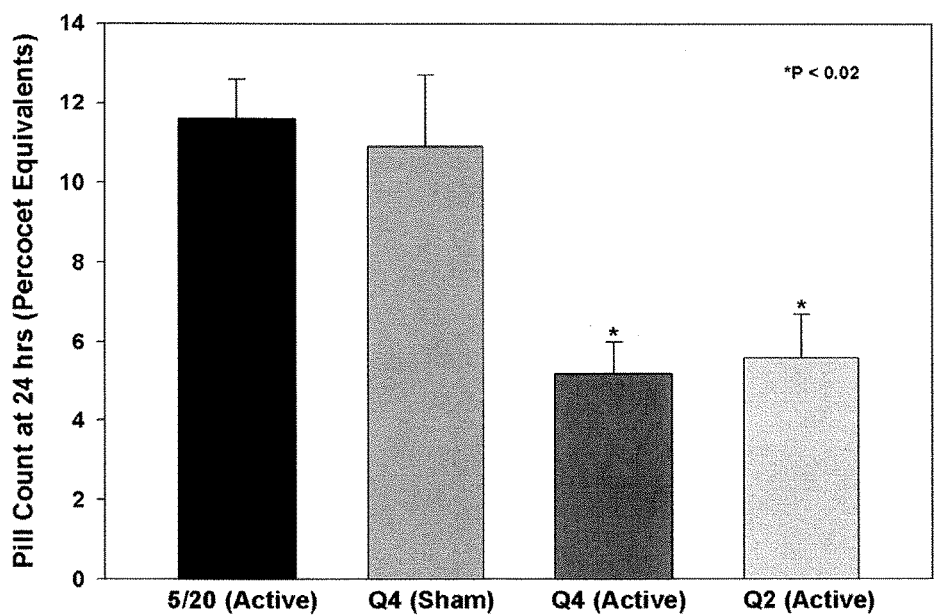
FIG. 5 is a graph showing the effect of different PEMF therapy regimens in accordance with the embodiments described herein on pain medication usage of patients after surgery. The results show approximately 2-fold more narcotic pills were taken by 24 h postoperatively in the Q4 (sham) and 5/20 (active) cohorts versus the Q4 (active) and Q2 (active) cohorts. There was no significant difference in postoperative narcotic use between the 5/20 (active) and Q4 (sham) cohorts.

Data from 50 patients were available for analysis. The change in VAS scores normalized to 1 h for each cohort is summarized in FIG. 4. The rate of postoperative pain decrease in the first 24 h postoperative for patients in the Q4 (active) and Q2 (active) cohorts was not significantly different (P=0.485), but was nearly 3-fold faster than that for patients in the 5/20 (active) and Q4 (sham) cohorts (P<0.01). In contrast, the rate of pain decrease for patients treated with the 5/20 (active) regimen was not significantly different from those receiving no PEMF treatment in the Q4 (sham) cohort (P=0.271). Specifically, pain at 24 h postoperative was, respectively, 43% and 35% of pain at 1 h postoperative for patients in the Q4 (active) and Q2 (active) cohorts (P<0.01). In contrast, pain at 24 h for patients in the 5/20 (active) cohort was 87% of pain at 1 h, compared with 74% for patients in the Q4 (sham) cohort (P=0.451). These results can be seen in FIG. 4. A similar pattern of results was found in narcotic usage. Postoperative narcotic usage by 24 h postoperative for patients in the 5/20 (active) cohort was not significantly different from that in the Q4 (sham) cohort (P=0.478), and both were approximately 2-fold higher compared with narcotic usage for patients in the Q4 (active) and Q2 (active) cohorts (P<0.02). Narcotic usage for patients in the Q2 (active) and Q4 (active) cohorts was not significantly different (P=0.246). These results can be seen in FIG. 5.

The identical PEMF signal configuration was used for all active cohorts; however, the dosing regimen was different. Entry criteria were identical for all patients. Surgery was performed by the same surgeon on all patients. The results clearly suggest that the effectiveness of PEMF therapy on the rate of postoperative pain decrease and post-operative narcotic requirements in BR patients depends on PEMF dosing regimen. A 5/20 (active) regimen was no different than the Q4 (sham) regimen for pain reduction, whereas a Q2 (active) regimen was as effective as the Q4 (active) regimen.

The findings revealed that the regimen of PEMF can significantly impact its effect on postoperative pain. It was expected that the most frequent dosing at 5 min every 20 min would have the greatest effect on pain reduction, but this was not the case. Mean VAS pain scores for patients in the 5/20 (active) cohort were not significantly different from those for patients in the Q4 (sham) cohort, which were more than two-fold higher at 24 h postoperatively than VAS scores for patients in the Q4 (active) and Q2 (active) cohorts. Similar comparative results were obtained for postoperative narcotic usage for patients in each of the active cohorts.

PEMF signal parameters, including repetition rate, were identical for all patients in active cohorts. The dosing change was treatment regimen. The rate of increase in CaM-dependent NO, and therefore cGMP, from PEMF in tissue for the 5/20 regimen is nearly 2.5-fold higher than that for the Q2 (active) and 4-fold higher than that for the Q4 (active) regimens. The NO/cGMP signaling pathway is a principal anti-inflammatory pathway. CaM-dependent PDE activity regulates this pathway by inhibiting cGMP. The PEMF signal used in this study is known to enhance NO/cGMP signaling, and to enhance CaM-dependent PDE activity [5-7]. It was proposed that the 5/20 regimen caused PDE activity to predominate, thereby inhibiting all the enhanced cGMP produced by PEMF. The result is no effect of PEMF on postoperative pain.

Two recent publications illustrate that PEMF effects depend on signal configuration. The first showed that the PEMF effect on breast cancer cell apoptosis was significant when the same waveform, applied for the same exposure time, repeated at 20 Hz but not at 50 Hz [35]. The second study showed that PEMF significantly reduced the expression of inflammatory markers, tumor necrosis factor, and nuclear factor-kappa beta in challenged macrophages when the same waveform, applied for the same exposure time, was repeated at 5 Hz, but not at 15 or 30 Hz [36]. In both studies, CaM-dependent NO/cGMP signaling modulates the expressions of these inflammatory markers [37,38], suggesting the effect of increased repetition rate is consistent with increased production of NO at a rate high enough for PDE inhibition of cGMP isoforms to predominate, thus blocking the PEMF effect. It is interesting to note that similar dosing effects have been observed in studies using low-level laser therapy, wherein the mechanism of action also involves NO/cGMP signaling [39]. Comparable with our study, low-level laser therapy improvement of neurologic performance in a mouse traumatic brain injury model depended on treatment regimen [40].

This study provides evidence that nonthermal radio frequency PEMF therapy can accelerate pain reduction and decrease pain medication requirements in the immediate postoperative period. The effect of PEMF regimen has been elucidated and effective regimens defined. Every 2 or 4 h dosing significantly decreases postoperative pain, whereas every 20-min dosing has no effect compared with placebo. The results of this study confirm dosing by which a given PEMF signal, configured to enhance the body's primary anti-inflammatory signaling pathway, CaM-dependent NO/cGMP, can accelerate postoperative pain relief.

At the cellular level the effect of PEMF signal configuration on PDE inhibition of cGMP was examined in cell cultures. Cells were plated in DMEM containing low concentration (challenge) of fetal calf-serum in 24-well plates. Two cell types were tested; human fibroblasts (HFC) and human chondrocytes (HCC). Cells were grown for 24-hours to allow for attachment and repair after initial plating. Cells were exposed to PEMF signals for 15 minutes. Immediately after treatment conditioned media (CM) was collected and assayed for NO levels using the Griess reaction combined with vanadium. The Griess assay tests for nitrite (NO2-). Vanadium was used to reduce nitrate (NO3-) to NO2- since NO immediately reacts with water to form NO3- and NO2- and the Griess assay only measures NO2-.

Two PEMF signals with 27.12 MHz sinusoidal carrier were tested. One PEMF signal had a burst width of 2 msec repeating at 2 Hz (Signal I) while the second signal (Signal II) had a burst width of 3 msec repeating at 5 Hz. Both signals were tested at amplitudes ranging from 0.5 to 8 µT. Exposure time was 15 min for each amplitude condition. Since each waveform was configured to target Ca/CaM binding, Signal II would be expected to produce approximately 4-fold more NO than that produced by Signal I, at all amplitudes studied.

Figure 6A:
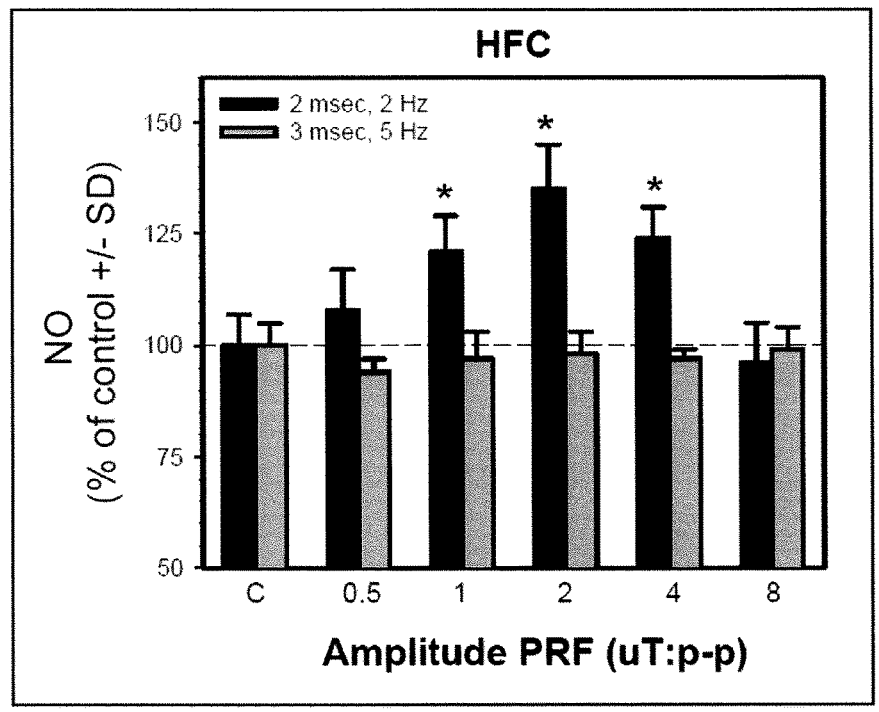
FIGS. 6A and 6B are graphs showing the effect of signal configuration on NO production from challenged fibroblasts and chondrocytes (respectively) in culture.
Figure 6B:
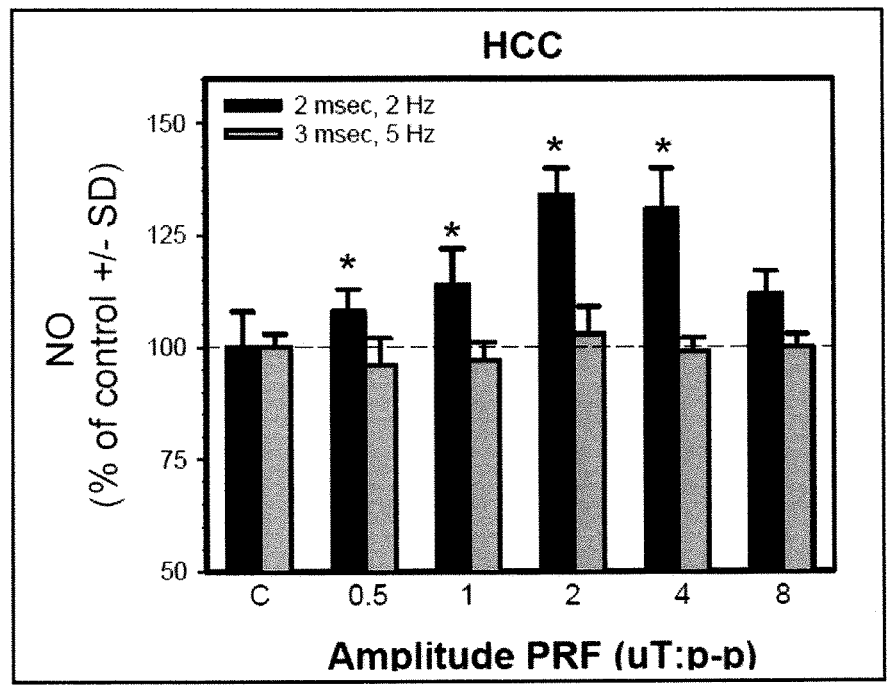

The results are shown in FIGS. 6A and 6B, wherein it may be seen that Signal I produced significant increases in NO over a range of amplitudes. In contrast, Signal II did not produce increased NO at any amplitude tested. As for the clinical example CaM-dependent PDE activity regulates NO/cGMP signaling by inhibiting cGMP. It was proposed that Signal II with increased burst duration and repetition rate compared to Signal I increased NO too rapidly causing the PEMF effect on PDE activity to predominate, thereby inhibiting all the enhanced NO produced by PEMF. The result is no effect of PEMF on NO release in challenged fibroblasts and chondrocytes for Signal II at any amplitude tested.

Figure 7:
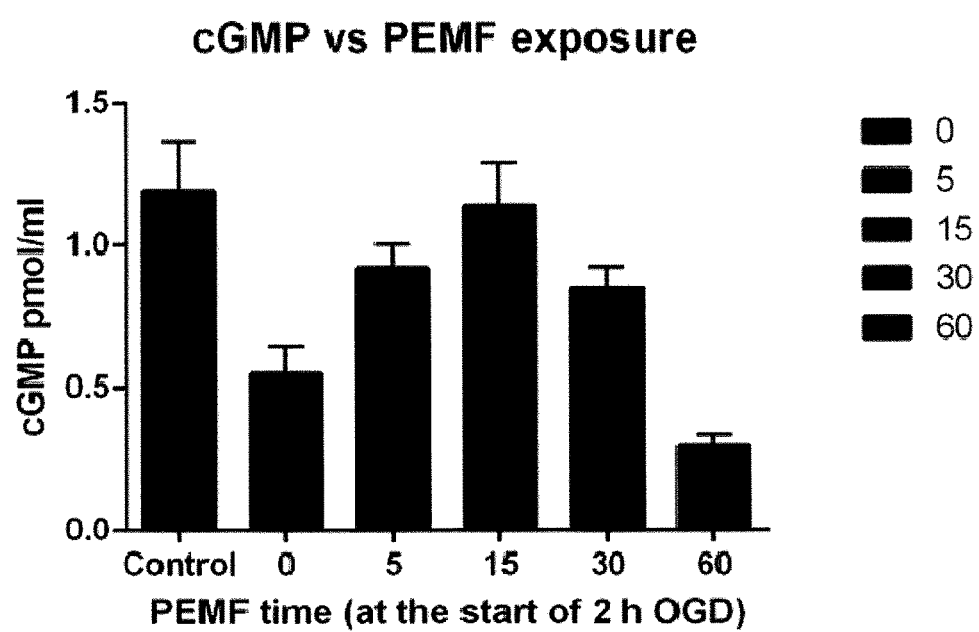
FIG. 7 is a graph showing the effect of exposure time of a given signal configuration on cGMP production in primary neuronal cells.

In another cellular study the effect of exposure time of a PEMF signal consisting of a 2 msec burst of a 27.12 MHz carrier repeating at 2 Hz and delivering 4 µT amplitude was tested. Primary neuronal cells were subjected to oxygen glucose deprivation (OGD) which subjects the cells to ischemic conditions such as those which exist in cardiac and brain ischemia. OGD is expected to reduce NO and therefore cGMP. The parameters of the PEMF signal were chosen to modulate CaM/NO/cGMP signaling so that exposure to PEMF during OGD would be expected to produce increased cGMP. However, as exposure time increases, the PEMF effect on PDE activity also increases. Referring to the results given in the previous clinical and cellular examples, an exposure time of 60 minutes would be expected to produce about 4-fold more NO than the standard effective 15 minute exposure. The results are shown in FIG. 7 wherein it may be seen that 15 minute PEMF exposure maximally restored cGMP production. In contrast, an exposure time of 60 minutes was not effective.

Therefore, in some embodiments any of the PEMF parameters can be selected to minimize the PDE inhibition of cGMP and/or maximize the production of cGMP. In some embodiments the length of the inter-treatment period and the length of the treatment interval are selected to minimize the PDE inhibition of cGMP. Any of the PEMF waveform parameters can be optimized in conjunction with the length of the treatment interval and inter-treatment period to achieve a desired change to the production of PDE and/or to decrease the inhibition of cGMP by PDE.

In the example shown in FIG. 1B, once treatment begins 103, the device, in some variations, applies an envelope of high-frequency waveforms at low amplitude (e.g. less than 50 milliGauss, less than 100 milliGauss, less than 200 milliGauss, etc.) 105. This envelope of high-frequency pulses is then repeated at a particular frequency (repetition rate) after an appropriate delay. The repetition rate may be varied to minimize PDE inhibition of PDE. The amplitude may be varied to minimize PDE inhibition of PDE. The burst duration may be varied to minimize PDE inhibition of PDE.

The initial signal configuration (burst duration, burst repetition and amplitude) can be repeated for a first treatment time and then followed by a delay during which the treatment is "off" 107. This waiting interval (inter-treatment interval) may last for minutes or hours and then the treatment interval may be repeated again until the treatment regime is complete 109.

In some embodiments the length of the inter-treatment period can be selected to minimize the PDE inhibition of cGMP. In some embodiments the inter-treatment period is greater than about 15 minutes. In some embodiments the inter-treatment period is greater than about 30 minutes. In some embodiments the inter-treatment period is greater than about 60 minutes. In some embodiments the inter-treatment period is greater than about 90 minutes. In some embodiments the inter-treatment period is greater than about 120 minutes. In some embodiments the inter-treatment period is greater than about 180 minutes. In some embodiments the inter-treatment period is greater than about 240 minutes In some embodiments the inter-treatment period can be expressed as a multiple of the PEMF treatment interval. In some embodiments the inter-treatment period is at least three times longer than the treatment interval. In some embodiments the inter-treatment period is at least four times longer than the treatment interval. In some embodiments the inter-treatment period is at least five times longer than the treatment interval. In some embodiments the inter-treatment period is at least six times longer than the treatment interval. In some embodiments the inter-treatment period is at least seven times longer than the treatment interval. In some embodiments the inter-treatment period is at least eight times longer than the treatment interval. In some embodiments the inter-treatment period is at least ten times longer than the treatment interval. In some embodiments the inter-treatment period is at least fifteen times longer than the treatment interval. In some embodiments the inter-treatment period is at least twenty times longer than the treatment interval.

Any of the PEMF treatment intervals disclosed herein can be used with any of the inter-treatment intervals disclosed herein. In some embodiments the treatment interval is about 5 minutes or longer. In some embodiments the treatment interval is about 10 minutes or longer. In some embodiments the treatment interval is about 15 minutes or longer. In some embodiments the treatment interval is about 20 minutes or longer.

In some embodiments the PEMF treatment period is five minutes with a 15 minute inter-treatment period. In some embodiments the PEMF treatment period is 15 minutes with a 105 minute inter-treatment period (e.g. 15 minutes of PEMF treatment per two hours). In some embodiments the PEMF treatment period is 20 minutes with a 160 minute inter-treatment period (e.g. 20 minutes of PEMF treatment per three hours).

In some variations, the treatment device is pre-programmed (or configured to receive pre-programming) to execute the entire treatment regime (including multiple on-periods and/or intra-treatment intervals) punctuated by predetermined off-periods (inter-treatment intervals) when no treatment is applied. In further variations, the device is pre-programmed to emit a PEMF signal at 27.12 MHz at 2 msec bursts repeating at 2 bursts/sec. In other embodiments, the device is pre-programed to emit a PEMF signal at 27.12 MHz (at about amplitude 250-400 mV/cm) pulsed in 4 msec bursts at 2 Hz.

In further variations, the method may include a pulsed electromagnetic field comprising a 2 msec burst of 27.12 MHz sinusoidal waves repeating at 2 Hz. In other variations, the method may include a pulsed electromagnetic field comprising a 3 msec burst of 27.12 MHz sinusoidal waves repeating at 2 Hz. In further embodiments, the pulsed electromagnetic field may comprise a 4 msec burst of 27.12 MHz sinusoidal waves repeating at 2 Hz.

The patient can be monitored during the PEMF treatment regime to determine the physiological response to the PEMF treatment regime. The treatment cycle (e.g. treatment period and inter-treatment period) can be repeated until a desired physiological response is achieved. Depending on the patient's response to the treatment, the subsequent treatment cycle parameters can be adjusted by a health professional to achieve a desired physiological response in the patient.

LIST OF REFERENCES CITED HEREIN

[1] Kehlet H, Wilmore D. Evidence-based surgical care and the evolution of fast-track surgery. Ann Surg 2008; 248: 189.

[2] Binshtok A M, Wang H, Zimmermann K, et al. Nociceptors are interleukin-1beta sensors. J Neurosci 2008; 28:14062.
[3] Pilla A A. Mechanisms and therapeutic applications of time varying and staticmagnetic fields. In: Barnes F, GreenebaumB, editors. Biological and Medical Aspects of Electromagnetic Fields. Boca Raton Fla.: CRC Press; 2007. p. 351.
[4] Pilla A A, Muehsam D J, Markov M S, Sisken B F. EMF signals and ion/ligand Binding kinetics: prediction of bioeffective waveform parameters. Bioelectrochem bioenerg 1999; 48:27.
[5] Pilla A, Fitzsimmons R, Muehsam D, Wu J, Rohde C, Casper D. Electromagnetic fields as first messenger in biological signaling: application to calmodulin-dependent signaling in tissue repair. Biochim Biophys Acta 2011; 1810:1236.
[6] Pilla A A. Electromagnetic fields instantaneously modulate nitric oxide signaling in challenged biological systems. Biochem Biophys Res Commun 2012; 426:330.
[7] Pilla A A. Nonthermal electromagnetic fields: from first messenger to therapeutic applications. Electromagn Biol Med 2013; 32:123.
[8] Ren K, Torres R. Role of interleukin-1beta during pain and inflammation. Brain Res Rev 2009; 60:57.
[9] Werner S, Grose R. Regulation of wound healing by growth factors and cytokines. Physiol Rev 2003; 83:835.
[10] Yen-Patton G P, Patton W F, Beer D M, et al. Endothelial cell response to pulsed electromagnetic fields: stimulation of growth rate and angiogenesis in vitro. J Cell Physiol 1988; 134:37.
[11] Tepper O M, Callaghan M J, Chang E I, et al. Electromagnetic fields increase in vitro and in vivo angiogenesis through endothelial release of FGF-2. FASEB J 2004; 18:1231.
[12] Callaghan M J, Chang E I, Seiser N, et al. Pulsed electromagnetic fields accelerate normal and diabetic wound healing by increasing endogenous FGF-2 release. Plast Reconstr Surg 2008; 121:130.
[13] Roland D, Ferder M S, Kothuru R, Faierman T, Strauch B. Effects of pulsed magnetic energy on a microsurgically transferred vessel. Plast Reconstr Surg 2000; 105:1371.
[14] Weber R V, Navarro A, Wu J K, Yu H L, Strauch B. Pulsed magnetic fields applied to a transferred arterial loop support the rat groin composite flap. Plast Reconstr Surg 2004; 114:1185.
[15] Delle Monache S, Alessandro R, Iorio R, Gualtieri G, Colonna R. Extremely low frequency electromagnetic fields (ELF-EMFs) induce in vitro angiogenesis process in human endothelial cells. Bioelectromagnetics 2008; 29:640.
[16] Rohde C, Chiang A, Adipoju O, Casper D, Pilla A A. Effects of pulsed electromagnetic fields on interleukin-1 beta and postoperative pain: a double-blind, placebo-controlled, pilot study in breast reduction patients. Plast Reconstr Surg 2010; 125:1620.
[17] Hede'n P, Pilla A A. Effects of pulsed electromagnetic fields on postoperative pain: a double-blind randomized pilot study in breast augmentation patients. Aesthet Plast Surg 2008; 32:660.
[18] Rawe I M, Lowenstein A, Barcelo C R, Genecov D G. Control of postoperative pain with a wearable continuously operating pulsed radiofrequency energy device: a preliminary study. Aesthet Plast Surg 2012; 36:458.
[19] Rohde C, Hardy K, Asherman J, Taylor E, Pilla A A. PEMF therapy rapidly reduces post-operative pain in TRAM flap patients. Plast Reconstr Surg 2012; 130:91.
[20] Strauch B, Herman C, Dabb R, Ignarro L J, Pilla A A. Evidencebased use of pulsed electromagnetic field therapy in clinical plastic surgery. Aesthet Surg J 2009; 29:135.
[21] Guo L, Kubat N J, Nelson T R, Isenberg R A. Meta-analysis of clinical efficacy of pulsed radio frequency energy treatment. Ann Surg 2012; 255:457.
[22] Batchelor A M, Bartus K, Reynell C, et al. Exquisite sensitivity to subsecond, picomolar nitric oxide transients conferred on cells by guanylyl cyclase-coupled receptors. Proc Natl Acad Sci USA 2010; 107:22060.
[23] Mo E, Amin H, Bianco I H, Garthwaite J. Kinetics of a cellular nitric oxide/cGMP/phosphodiesterase-5 pathway. J Biol Chem 2004; 279:26149.
[24] Miller C L, Oikawa M, Cai Y, et al. Role of Ca21p/calmodulin stimulated cyclic nucleotide phosphodiesterase 1 in mediating cardiomyocyte hypertrophy. Circ Res 2009; 105: 956.
[25] Li Wan Po A, Petersen B. How high should total pain-relief score be to obviate the need for analgesic remedication in acute pain? Estimation using signal detection theory and individual-patient meta-analysis. J Clin Pharm Ther 2006; 31:161.
[26] Wise R J. A preliminary report on a method of planning the mammaplasty. Plast Reconstr Surg 1956; 17:367.
[27] Karp N S. Medial pedicle/vertical breast reduction made easy: the importance of complete inferior glandular resection. Ann Plast Surg 2004; 52:458.
[28] Davison S P, Mesbahi A N, Ducic I, Sarcia M, Dayan J, Spear S L. The versatility of the superomedial pedicle with various skin reduction patterns. Plast Reconstr Surg 2007; 120:1466.
[29] Rasouli J, Lekhraj R, White N M, et al. Attenuation of interleukin-1beta by pulsed electromagnetic fields after traumatic brain injury. Neurosci Lett 2012; 519:4.
[30] McLeod B R, Pilla A A, Sampsel M W. Electromagnetic fields induced by Helmholtz aiding coils inside saline-filled boundaries. Bioelectromagnetics 1983; 4:357.
[31] Panagopoulos D J, Johansson O, Carlo G L. Evaluation of specific absorption rate as a dosimetric quantity for electromagnetic fields bioeffects. PLoS One 2013; 8: e62663.
[32] Coll A M, Ameen J R, Mead D. Postoperative pain assessment tools in day surgery: literature review. J Adv Nurs 2004; 46:124.
[33] Bodian C A, Freedman G, Hossain S, Eisenkraft J B, Beilin Y. The visual analog scale for pain: clinical significance in postoperative patients. Anesthesiology 2001; 95:1356.
[34] Lacy C F, Armstrong L L, Goldman M P, et al. Drug Information Handbook. 15th ed. Hudson, O H: Lexicomp; 2007.
[35] Crocetti S, Beyer C, Schade G, Egli M, Fro hlich J, Franco-Obrego'n A. Low intensity and frequency pulsed electromagnetic fields selectively impair breast cancer cell viability. PLoS One 2013; 8:e72944.
[36] Ross C L, Harrison B S. Effect of pulsed electromagnetic field on inflammatory pathway markers in RAW 264.7 murine macrophages. J Inflamm Res 2013; 6:45.
[37] Yurdagul A Jr, Chen J, Funk S D, Albert P, Kevil C G, On A W. Altered nitric oxide production mediates matrix-specific PAK2 and NF-kB activation by flow. Mol Biol Cell 2013; 24:398.
[38] Ha K S, Kim K M, Kwon Y G, et al. Nitric oxide prevents 6-hydroxydopamine-induced apoptosis in PC12 cells through cGMP-dependent PI3 kinase/Akt activation. FASEB J 2003; 17:1036.

[39] Chung H, Dai T, Sharma S K, Huang Y Y, Carroll J D, Hamblin M R. The nuts and bolts of low-level laser (light) therapy. Ann Biomed Eng 2012; 40:516.

[40] Xuan W, Vatansever F, Huang L, et al. Transcranial low-level laser therapy improves neurological performance in traumatic brain injury in mice: effect of treatment repetition regimen. PLoS One 2013; 8:e53454.

[41] Liu S S, Richman J M, Thirlby R C, Wu C L. Efficacy of continuous wound catheters delivering local anesthetic for postoperative analgesia: a quantitative and qualitative systematic review of randomized controlled trials. J Am Coll Surg 2006; 203:914.

[42] Taylor, Hardy, Alonso, Pilla, and Rhode, "Pulsed Electromagnetic Fields Dosing Impacts Postoperative Pain in Breast Reduction Patients", Journal of Surgical Research (2014) Oct. 9, 2014.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for treating a patient, the method comprising:
generating a pulsed electromagnetic field from a pulsed electromagnetic field source wherein the pulsed electromagnetic field consists of a burst having a duration of greater than 2 msec of a 27.12 MHz carrier repeating at between 1 and 20 bursts/sec at an amplitude of between 2 and 10 µT;
applying the pulsed electromagnetic field in proximity to a target region affected by an injury or condition to reduce a physiological response to the injury or condition for a treatment interval that is greater than or equal to 10 minutes;
discontinuing the application of the pulsed electromagnetic field for an inter-treatment period that is greater than six times the treatment interval; and
repeating, for a plurality of times, the steps of generating, applying and discontinuing.

2. The method of claim 1, further comprising increasing a rate of ion-dependent signaling and minimizing a rate of inhibition of said ion-dependent signaling by natural compounds.

3. The method of claim 1, further comprising increasing a rate of cyclic guanosine monophosphate (cGMP) signaling and minimizing a rate of inhibition of said cGMP signaling by compounds including phosphodiesterase (PDE).

4. The method of claim 1, further comprising increasing a rate of cyclic guanosine monophosphate (cGMP) signaling and minimizing a rate of inhibition of said cGMP signaling by compounds including phosphodiesterase (PDE).

5. The method of claim 1, wherein said repeating comprises repeating for at least 10 times.

6. The method of claim 1, wherein said repeating comprises repeating the steps of generating, applying and discontinuing, further wherein the pulsed electromagnetic field generated with each repetition is the same.

7. The method of claim 1, wherein the treatment interval is between 10 and 30 minutes.

8. The method of claim 1, wherein the inter-treatment period is greater than seven times the treatment interval.

9. The method of claim 1, wherein the inter-treatment period is between six and 100 times the treatment interval.

10. The method of claim 1, wherein the inter-treatment period is greater than or equal to 90 minutes.

11. The method of claim 1, wherein the inter-treatment period is greater than or equal to 180 minutes.

12. The method of claim 1, wherein the length of a first treatment interval and the length of the inter-treatment period are selected to minimize phosphodiesterase (PDE) production in the patient.

13. The method of claim 1, further comprising
monitoring the physiological response; and
modifying the pulsed electromagnetic field in response to the monitoring step.

14. The method of claim 1, further comprising
monitoring the physiological response; and
discontinuing treatment once an acceptable level of the physiological response is reached.

15. The method of claim 1, further comprising modulating inflammatory cytokines and growth factors at the target region by applying the pulsed electromagnetic field to simultaneously increase the rate of said modulation and to minimize the rate of inhibition of modulation by natural compounds.

16. The method of claim 1, further comprising accelerating healing of the target region by applying the pulsed electromagnetic field to simultaneously increase a rate of healing and to minimize a rate of inhibition of such healing.

17. The method of claim 1, wherein applying the pulsed electromagnetic field in proximity to the target region affected by the neurological injury or condition to reduce the physiological response comprises reducing a concentration of interleukin-1beta (IL-1β).

18. The method of claim 17, wherein the neurodegenerative disease is Parkinson's disease or Alzheimer's disease.

19. The method of claim 1, wherein the injury or condition is a neurodegenerative disease.

20. The method of claim 1, wherein the injury or condition is traumatic brain injury (TBI).

21. The method of claim 1, wherein the injury or condition is post-operative inflammation and pain.

22. A method for treating a patient, the method comprising:
generating a pulsed electromagnetic field from a pulsed electromagnetic field source wherein the pulsed electromagnetic field consists of a burst having a duration of between 2 and 10 msec of a carrier wave repeating at between 1 and 10 bursts/sec at an amplitude of between 3 and 8µT;
applying the pulsed electromagnetic field in proximity to a target region affected by an injury or condition to reduce a physiological response to the injury or condition for a treatment interval that is greater than 10 minutes;
discontinuing the application of the pulsed electromagnetic field for an inter-treatment period that is greater than six times the treatment interval; and
repeating, for a plurality of times, the steps of generating, applying and discontinuing.

* * * * *